(12) United States Patent
Bokan et al.

(10) Patent No.: US 10,076,260 B2
(45) Date of Patent: *Sep. 18, 2018

(54) INTEGRATED ANALYSIS OF ELECTROPHYSIOLOGICAL DATA

(71) Applicant: CARDIOINSIGHT TECHNOLOGIES, INC., Independence, OH (US)

(72) Inventors: Ryan Bokan, Cleveland, OH (US); Charulatha Ramanathan, Solon, OH (US); Ping Jia, Solon, OH (US); Maria Strom, Moreland Hills, OH (US); Qingguo Zeng, Solon, OH (US)

(73) Assignee: Cardioinsight Technologies, Inc., Independence, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/711,642

(22) Filed: Sep. 21, 2017

(65) Prior Publication Data

US 2018/0042507 A1 Feb. 15, 2018

Related U.S. Application Data

(63) Continuation of application No. 14/614,219, filed on Feb. 4, 2015, now Pat. No. 9,820,666.

(Continued)

(51) Int. Cl.
*A61B 5/0452* (2006.01)
*A61B 5/024* (2006.01)
(Continued)

(52) U.S. Cl.
CPC .......... *A61B 5/0452* (2013.01); *A61B 5/0245* (2013.01); *A61B 5/02405* (2013.01); *A61B 5/04012* (2013.01); *A61B 5/044* (2013.01)

(58) Field of Classification Search
CPC ................. A61B 5/044; A61B 5/046–5/0472
See application file for complete search history.

(56) References Cited

U.S. PATENT DOCUMENTS 9,820,666 B2 * 11/2017 Bokan ............... A61B 5/044
2002/0128565 A1 9/2002 Rudy
(Continued)

FOREIGN PATENT DOCUMENTS

WO 2012151498 A2 11/2012
WO 2013006713 A2 10/2013

OTHER PUBLICATIONS

European Application No. EP15746738, Filed: Feb. 4, 2015; Applicant: CardioInsight Technologies, Inc.; Supplementary European Search Report, Examiner: Stephane Furlan, Dae of Completion of the Search: Sep. 8, 2017; 7 pp.

(Continued)

*Primary Examiner* — George Evanisko
(74) *Attorney, Agent, or Firm* — Tarolli, Sundheim, Covell & Tummino LLP

(57) ABSTRACT

A method can include analyzing non-invasive electrical data for a region of interest (ROI) of a patient's anatomical structure to identify one or more zones within the ROI that contain at least one mechanism of distinct arrhythmogenic electrical activity. The method also includes analyzing invasive electrical data for a plurality of signals of interest at different spatial sites within each of the identified zones to determine intracardiac signal characteristics for the plurality of sites within each respective zone. The method also includes generating an output that integrates the at least one mechanism of distinct arrhythmogenic electrical activity for the one or more zones with intracardiac signal characteristics for the plurality of sites within each respective zone.

17 Claims, 13 Drawing Sheets

Related U.S. Application Data

(60) Provisional application No. 61/935,620, filed on Feb. 4, 2014.

(51) Int. Cl.
*A61B 5/0245* (2006.01)
*A61B 5/04* (2006.01)
*A61B 5/044* (2006.01)

(56) References Cited

U.S. PATENT DOCUMENTS

| | | |
|---|---|---|
| 2004/0059237 A1 | 3/2004 | Narayan et al. |
| 2008/0058657 A1 | 3/2008 | Schwartz |
| 2011/0144510 A1 | 6/2011 | Ryu et al. |
| 2013/0006713 A1 | 1/2013 | Haake |
| 2013/0116681 A1 | 5/2013 | Zhang |
| 2013/0131529 A1 | 5/2013 | Jia et al. |
| 2015/0032051 A1 | 11/2015 | Edwards |
| 2015/0320515 A1* | 11/2015 | Edwards ............ A61B 19/5244 600/389 |

OTHER PUBLICATIONS

Applicant: CardioInsight Technologies,Inc., International Application No. PCT/US2015/014480; Filed Feb. 4, 2015, International Search Report and Written Opinion, Authorized Oficer: Blaine R. Coopenheaver, Date of Completion: Apr. 10, 2015; pp. 6.

* cited by examiner

INTEGRATED ANALYSIS OF ELECTROPHYSIOLOGICAL DATA

CROSS-REFERENCE TO RELATED APPLICATION

This application claims the benefit of U.S. patent application Ser. No. 14/614,219, filed Feb. 4, 2015, and entitled INTEGRATED ANALYSIS OF ELECTROPHYSIOLOGICAL DATA, which claims the benefit of U.S. Provisional Patent Application No. 61/935,620, filed Feb. 4, 2014, and entitled INTEGRATION OF INVASIVE AND NONINVASIVE SIGNALS, both which are incorporated herein by reference in its entirety.

TECHNICAL FIELD

This disclosure relates to integrated analysis of electrophysiological data.

BACKGROUND

During an electrophysiological (EP) diagnostic procedure (also called EP study), catheters are strategically placed at various locations of the heart to provide signals, which are displayed as traces on a recording system. An EP recording system allows an orderly display of these recordings in the format of individual traces; each trace corresponding to an electrode (catheter electrode/pair or ECG electrode). Systems employing non-fluoroscopic navigation systems like CARTO® and NavX® have been developed to create the geometry of the cardiac chambers of interest and provide a color-coded display of the activation times or potential amplitudes. The systems have several technical limitations, including requiring a lot of manual editing of activation times, inaccurate geometry, instability and shifts in the points over time. The systems also have several clinical limitations including inability to map unstable, intermittent arrhythmias, inability to simultaneously map bi-chamber (or whole heart), and inability to effectively map complex rhythms with varying cycle lengths like atrial fibrillation.

BRIEF DESCRIPTION OF THE DRAWINGS

FIG. 10 depicts examples of signals for different spatial sites demonstrating periods of AF and AT and conduction pattern for the coronary sinus signals.

SUMMARY

Figure 1:
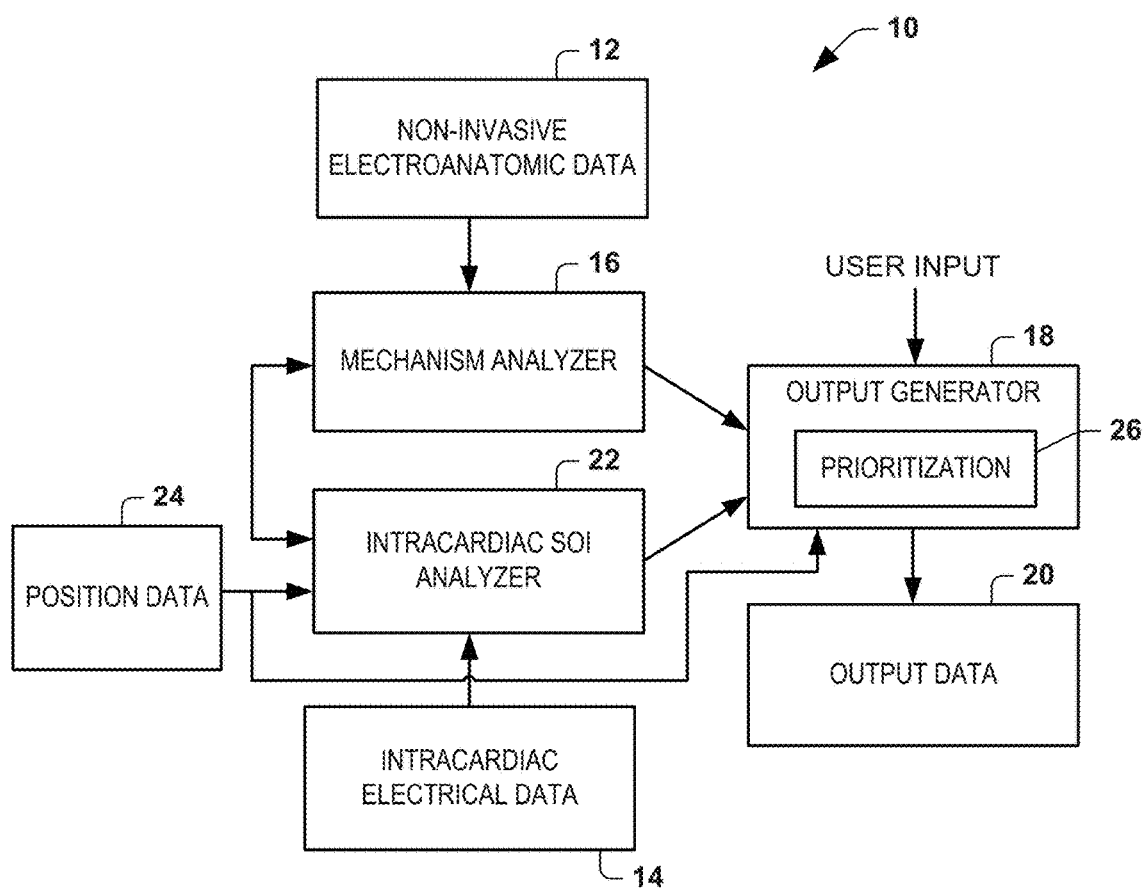
FIG. 1 depicts an example of block diagram demonstrating an overview of a system for integrating invasively and non-invasively information.

This disclosure relates to integrated analysis of electrophysiological data.

In one example, a method includes analyzing non-invasive electrical data for a region of interest (ROI) of a patient's anatomical structure to identify one or more zones within the ROI that contain at least one mechanism of distinct arrhythmogenic electrical activity. The method also includes analyzing invasive electrical data for a plurality of signals of interest at different spatial sites within each of the identified zones to determine intracardiac signal characteristics for the plurality of sites within each respective zone. The method also includes generating an output that integrates the at least one mechanism of distinct arrhythmogenic electrical activity for the one or more zones with intracardiac signal characteristics for the plurality of sites within each respective zone.

As another example, as system includes memory to store non-invasive electroanatomic data representing cardiac electrical activity reconstructed on a cardiac envelope based on non-invasively sensed electrical data and intracardiac electrical data based on invasively measured electrical data for a plurality of sites. The system can include machine readable instructions executable by a processor. The instructions include an mechanism analyzer to provide zone data identifying one or more zones within a region of interest of the cardiac envelope that contain at least one mechanism of distinct arrhythmogenic electrical activity based on non-invasively sensed electrical data. An intracardiac analyzer determines intracardiac signal characteristic data representing intracardiac signal characteristics based on the intracardiac electrical data for a plurality of sites within each respective zone. An output generator provides output data that integrates the zone data and the intracardiac signal characteristic data in a hybrid graphical map.

DETAILED DESCRIPTION

This disclosure relates to integrated analysis of electrophysiological data. Systems and methods can be utilized to help diagnose and facilitate treatment cardiac disease and disorder, such as arrhythmias. The systems and methods disclosed herein are adapted to integrate non-invasive electroanatomic data (e.g., derived from body surface measurements of electrical activity) with intracardiac electrical data (e.g., obtained invasively or derived in part from invasively obtained data) to detect and characterize one or more arrhythmia drivers to facilitate diagnosis and/or treatment of such identified drivers.

By way of example, systems and methods disclosed herein can integrate non-invasive electrical anatomic data with intracardiac electrical data to determine a priority for an anatomical region of interest (e.g., one or more areas across a cardiac envelope up to including the entire cardiac surface). For example, an indication of synchrony for the anatomical region of interest can be utilized to determine which chamber, or a spatial region within a chamber, is most disorganized (least synchronized) and therefore should be afforded a higher priority. Additionally, one or more zones are identified based on detecting one or more mechanisms of distinct arrhythmogenic electrical activity (e.g., arrhythmia mechanisms). The zones can reside in the chamber and/or region of interest within a chamber determined to be disorganized. The zones can be defined according to spatial geometry and/or temporal (e.g., one or more time intervals) where the arrhythmia mechanism are identified across one or more regions of interest for the patient's anatomical structure, which can include one or more area across a cardiac envelope up to including the entire cardiac envelope.

Intracardiac electrical data can be stored in memory based on signals measured directly (e.g., from a mapping catheter or similar invasive sensing device or derived from a combination of invasive and non-invasive electrical measurements) at a plurality of points contained within the identified zones for the patient's anatomical structure (e.g., a patient's heart). The intracardiac measurements can be obtained before, during or after the non-invasive measurements. The Intracardiac electrical data is analyzed to determine one or more cardiac signal characteristics for a plurality of sites within each of the zones, which have been identified based on the analysis of the non-invasive electrical data. Thus, by including the global synchrony analysis in combination with identifying zones that reside within or are near non-synchronization regions, the approach helps ensure that the zones being prioritized are most likely causing the arrhythmia. The further localized evaluation of intracardiac signals of interest information further facilitates the prioritization.

As a further example, the intracardiac signal characteristics and mechanisms of distinct arrhythmogenic electrical activity can further be evaluated to determine the priority among sites within the respective zones. For instance, the priority can specify a recommended treatment order for the various sites within the identified zones. In some examples, the intracardiac signal characteristics can be weighted differently, such as depending upon the mechanisms that have been identified for the zones in which measurements were made corresponding to the signals of interest. The computed mechanisms of distinct arrhythmogenic electrical activity in each zone and/or the intracardiac statistics further can be employed as part of a treatment workflow procedure to identify priority, progress and, in some cases, an endpoint for treatment at a given cardiac signal or zone. During or following treatment, for example, a user can confirm a positive change in one or more intracardiac characteristics, confirm a decrease in mechanisms (e.g, by remapping across the cardiac envelope, as well as evaluate global changes in synchrony across the cardiac envelope. For example, in response to determining improvement at the selected site residing in the given zone based on comparing an indication of synchrony across atria or regions of interest near to the given zone identified prior to applying the therapy with respect to synchrony across the atria or the regions of interest near to the given zone identified following the applying the treatment to the selected site. By integrating non-invasive information with intracardiac information can provide accurate information that is clinical relevant that can translate to improved outcomes, including for treating complex arrhythmias like fibrillation.

The disclosure also includes concepts to provide hybrid visualization of the relevant spatio-temporal characteristics of intra-cardiac electrograms along with the maps/information provided by electrocardiographic mapping from the non-invasive data. The systems and methods disclosed herein can thus incorporate the strengths of a conventional EP study with a 3D mapping system while providing both epicardial, endocardial and whole heart mapping information in a beat to beat fashion for all arrhythmias including fibrillation. In examples when the hybrid systems and methods are utilized intraoperatively during a procedure, the graphical maps of the heart electrical activity can provide an integrated graphical visualization of the mechanisms and intracardiac signal characteristics that have been determined based on the non-invasive and invasive information.

In some examples herein, the electrophysiological data includes non-invasive data derived from non-invasive sensors and intracardiac data measured from one or more invasive sensors positioned within a patient's body. While the electrophysiological data (intracardiac data and non-invasive data) can be based on sensed electrical activity, which can be measured invasively or non-invasively, the system and methods disclosed herein do not require any human interaction or particular source of information since the systems and methods process data that has been stored in memory without consideration of where such data actually originates and further does not require any treatment or interaction with a patient to perform the functions and methods disclosed herein. Thus the systems and methods disclosed herein can be implemented as machine readable instructions stored in memory which can be accessed by and executed by one or more processing units.

FIG. 1 depicts an example of a system 10 to integrate analysis of non-invasively acquired electrical data and invasively acquired intracardiac information. Thus in the example of FIG. 1, the system 10 includes non-invasive electroanatomic data 12 and intracardiac electrical data 14. For example, the non-invasive electroanatomic data 12 can include data representing electrograms on a cardiac envelope computed based on measurements of body surface electrical activity by a plurality of sensors distributed across a patient's torso, such as disclosed herein. The non-invasive electroanatomic data 12 can correspond to data acquired previously (e.g., in a prior electrophysiological study) over one or more time intervals. Alternatively or additionally, the non-invasive electroanatomic data 12 can correspond to real time data as it is being acquired from a patient based on an arrangement of sensors distributed across the body surface of a patient (e.g., the patient's thorax or a substantial portion of the patient's thorax). In some examples, the non-invasive electroanatomic data 12 can correspond to reconstructed electrograms across the entire surface of a patient's heart or other cardiac envelope. As used herein, the cardiac envelope can correspond to any three dimensional surface geometry onto which the electrical signals from the body surface sensors are reconstructed by computing the inverse solution based on the sensed signals and geometry data, such as disclosed herein. The cardiac envelope can be an epicardial surface (e.g., estimated from imagining data or another model) or an endocardial surface. Alternatively or additionally, the cardiac envelope can correspond to a geometric surface that resides between the epicardial surface of a patient's heart and the surface of the patient's body where the sensor array has been positioned.

A mechanism analyzer 16 is programmed to analyze the non-invasive electroanatomic data 12 for a region of interest (ROI) of the patient's anatomical structure (e.g., the entire heart, another cardiac envelope or one or more portions thereof). The mechanism analyzer 16 can identify one or more zones within the ROI that contain one or more mechanism of distinct arrhythmogenic electrical activity. As used herein, mechanisms of irregular activity can correspond to any biological or electrical mechanism that may drive or contribute to distinct arrhythmogenic electrical activity, such as cardiac arrhythmias. There can be any number of one or more mechanisms for a given arrhythmia, which are the underlying cause or contributed to the arrhythmia. Examples of mechanisms of distinct arrhythmogenic electrical activity can include rotors, focal points, and areas of fast (e.g., bursting) cycle length, inter-chamber synchrony as well as intra-chamber synchrony. The mechanism analyzer 16 can also characterize each of the identified mechanisms or groups of such mechanisms. As disclosed herein, for example, the mechanism analyzer 16 can be programmed to compute an indication of sustainability (e.g., a sustainability index) for one or more mechanisms that have been identified for a time interval, such as based on the number of mechanisms and the average sustainability of such mechanisms.

As used herein "distinct arrhythmogenic electrical activity" and variations thereof refer to any one or more detectable conditions in which electrophysiological signals or information derived from such signals exhibits something other than a normal condition, which can be disorganized, irregular, faster or slower than normal, as compared to a baseline for the patient or a corresponding patient population. Examples of arrhythmogenic electrical activity thus can include an arrhythmia for a point or region of an anatomical structure (e.g., heart, brain, etc.), such as can include bradycardia, atrial tachycardia, atrial flutter, atrial fibrillation, atrial-ventricular nodal reentrant tachycardia (AVNRT), atrial-ventricular reciprocating tachycardia (AVRT), ventricular tachycardia, ventricular flutter and ventricular fibrillation. Additionally or alternatively, arrhythmogenic electrical activity also can encompass irregular or dyssynchronous electrical activity across one or more regions, which can include spatial regions within different chambers or different regions within a common chamber. A defined area on the cardiac envelope that contains one or more such detected mechanisms of distinct arrhythmogenic electrical activity that occur during a time interval defines a corresponding zone.

The mechanism analyzer 16 can identify each zone containing one or more mechanisms and provide zone data to an output generator 18. The zone data can specify a number of mechanisms that occur within a given zone during a corresponding time interval as well as the type of each respective mechanism that has been identified in each zone during the respective time intervals. The output generator 18 can provide associated output data 20 to graphically represent the zones in a graphical map. For example, one or more zones (each containing one or more mechanisms) can be identified in a 3D map as a spatial area having a particular color or other encoding to identify the spatial region as a zone. In some examples, the number and type of each mechanism also can be identified (e.g., via color coding or other annotation) on the graphical map of the anatomical surface.

As an example, in response to a user input selecting an interactive graphical user interface (GUI) element corresponding to a zone with a pointing element or hovering a pointing element over the zone GUI element, the output generator 18 can provide an indication of the number and type of mechanisms that have been identified for each respective zone as well as other characteristics for such mechanisms (e.g., an indication of mechanism sustainability).

In some examples, different colors or other visual or text based indicators can be presented based on the output data. For example, the output generator 18 can be configured to employ a color scale to graphically differentiate each of the zones that have been identified by the mechanism analyzer 16 relative to other parts of the graphical map containing a depiction of the 3D map of the heart.

As mentioned, the non-invasive electroanatomic data 12 can be derived from non-invasive measurements obtained from an arrangement of sensors position over a surface of a patient's body. In addition, the system 10 can implement sophisticated signal processing techniques to map transient, intermittent, unstable arrhythmias including varying cycle length arrhythmias like atrial and ventricular fibrillation, for example. The output data 20 provided by the system 10 can also provides an interactive display of 3D maps and unipolar electrograms in one or more formats familiar to electrophysiologists. The output generator 18 further can generate the output data based on the electroanatomic data 12 as well as the intracardiac data 14 to provide highly accurate bi-atrial, bi-ventricular or whole heart anatomic cardiac maps, such as on detailed cardiac geometries.

The system 10 can also include an intracardiac signal of interest (SOI) analyzer 22 to analyze the intracardiac electrical data 14 for each of a plurality of SOI at different spatial sites associated with one or more of the zones identified by the mechanism analyzer 16. The intracardiac SOI analyzer 22 thus employs the intracardiac electrical data 14 to determine one or more intracardiac signal characteristics for each of a plurality of sites where measurements are obtained. For example, the intracardiac SOI analyzer 22 can process the SOIs fort each site to calculate the intracardiac signal characteristics to include one or more of cycle length, cycle length variation, percentage of continuous activation, activation slope and fractionation determined from one or more measurement interval for the SOIs at each of the sites. The measurement interval can be the time period during which electrical measurements are obtained invasively directly for each cardiac site one or more sensors positioned within the patient's body. The sensors can be direct contact sensors that contact the surface of a patient' heart or noncontact sensors that detect the electrical activity invasively but without contacting the surface of the heart (e.g., epicardially or endocardially).

The output generator 18 thus can be programmed to generate output data 20 that integrates the zone data, corresponding to one or more mechanisms of distinct arrhythmogenic electrical activity for one or more zones, with intracardiac signal characteristic data, corresponding to intracardiac signal characteristics for the plurality of sites within each respective zone. For instance, the integrated output data can be provided as a hybrid graphical map of cardiac electrical activity superimposed on a model of heart, which combines global beat-to-beat non-invasive mapping with information derived from direct intracardiac measurements.

In some examples, the intracardiac electrical data 14 can be derived based on a combination of invasively obtained measurements and reconstructed electrical signals derived from non-invasive body surface measurements. For example, by comparing and correlating physiological signal characteristics (e.g., activation times, repolarization times, signal amplitudes, and the like) from invasive measurements and reconstructed electrical signals at the same or approximately the same spatial locations over one or more of the common time intervals, a transformation can be determined that can be applied to the reconstructed electrical signals. Such transform can be stored in memory and applied to subsequent reconstructed electrical signals (e.g., electrograms) at the same or approximately the same location to convert such electrograms to simulate directly measured signals at the same location. For example, the transform can impose time shifting of morphological signal components, such as activation times, to align with measured activation times at respective local sites. Similar transforms can be computed and applied to convert reconstructed signals at each of the signals of the measurement sites into surrogates for corresponding intracardiac signals. As additional measurements are made at such sites or new sites transforms can be updated or generated accordingly.

Figure 5:
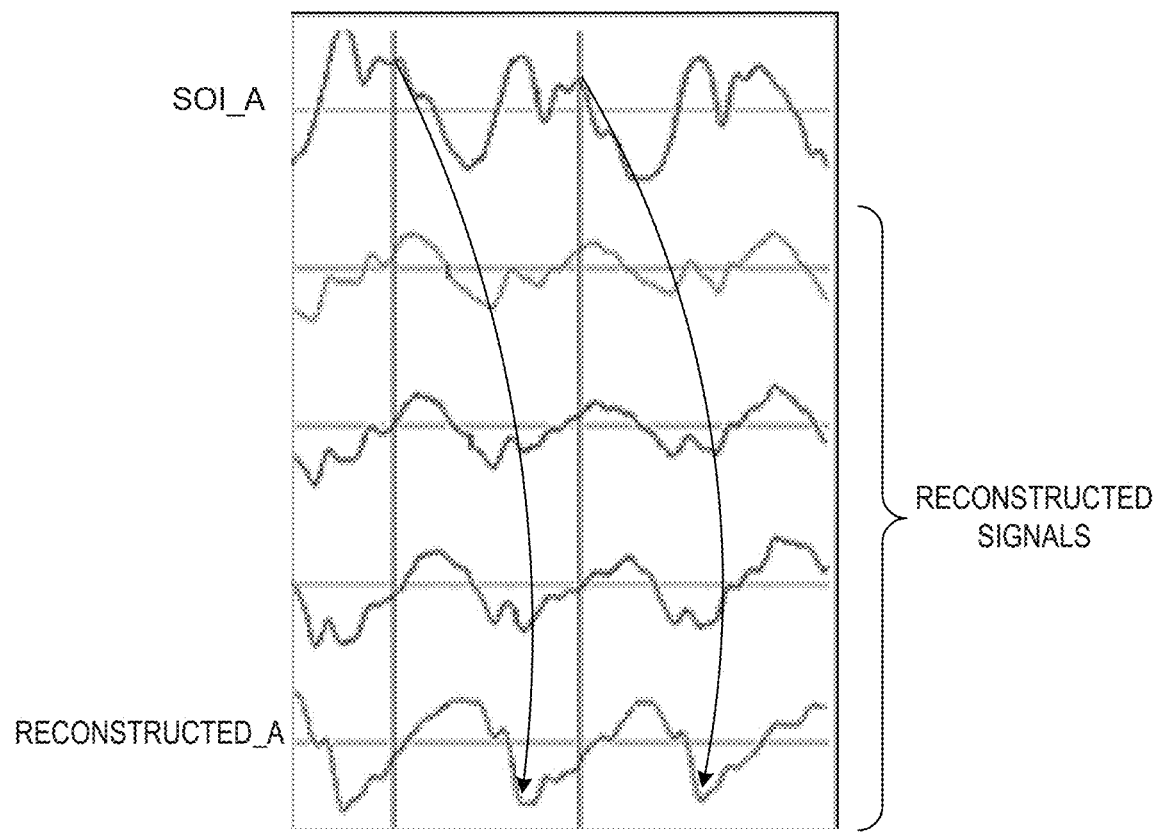
FIG. 5 depicts an example of signals demonstrating part of a calibration process between invasive signal of interest and a reconstructed signal.

FIG. 5 depicts an example of signals demonstrating calibration of an activation time between a measured signal of interest (SOI_A) for a given measurement interval and a corresponding reconstructed electrogram (RECONSTRUCTED_A) for the same location and time interval. Other reconstructed electrograms could be for random or nearby locations across the cardiac envelope. The relationships between activation times can be stored as the transform and applied to subsequent reconstructed electrograms to provide the surrogate reconstructed intracardiac signals at site A.

It is understood that the calibration can be implemented with respect to any any types of intracardiac signals measured at a known spatial location. Equally if not more relevant for organized arrhythmias. For example, in a given region of the cardiac envelope, a user can link a given intracardiac electrogram to a reconstructed unipolar electrogram that is spatially and temporally consistent. The linking, which can be automated or in response to a user input, can further use the intracardiac electrogram to define the activation time for the reconstructed electrogram. This allows the reconstructed electrogram to be a surrogate to intracardiac activation timing such that invasive measurements for the location are unnecessary to determine intracardiac activation timing.

As a further example, the intracardiac SOI analyzer 22 can compute values for the intracardiac signal characteristics based on statistical analysis of the characteristics calculated over a period of time such as can include the one or more measurement intervals for each site or a selected one or more portions thereof for each site (e.g., selected in response to a user input or automatically). For instance, cycle length can be computed for an SOI at a given site based on the time interval between each pair of consecutive activation times for the given site, which cycle length time values for the SOI can be averaged over time (e.g., the sum of the cycle lengths) to provide an average or median cycle length for each site. The cycle length variation can be determined as the standard deviation of the cycle length time values that have been computed for each SOI. Other signal characteristics (e.g., statistical information) can be computed for each SOI such as disclosed herein.

As a further example, the intracardiac SOI analyzer 22 can compute statistics for the intracardiac signal characteristics at respective SOIs that depend on the mechanisms identified for the zone in which the SOIs reside. The representative SOI statistic for a given zone can be customized to reflect the one or more mechanisms detected for the given zone. If, for example, zone1 has 80% rotor, 20% foci, and SOI statistic A is representative of rotor and SOI statistic B is representative of foci, the intracardiac SOI output can reflect A 80% and B 20%. In this way, the system can compute and weight statistics to represent the identified mechanisms, which are determined from non-invasive electroanatomic data The intracardiac electrical data 14 can correspond to data that has been obtained concurrently with or after the non-invasive electronatomical data 12 has been generated. In order to facilitate collection of the intracardiac electrical data 14, a corresponding navigation or localization system can be utilized to provide position data 24. The position data 24 can be provided to the output generator 18 which can be utilized to generate the output data 20 that can include an indication (e.g., a graphical representation) of the location of the sensors or other device that is being utilized to make the direct measurements from invasively in the patient's body to provide the intracardiac electrical data. The position data 24 can also be encoded into the intracardiac signal characteristics determined by the SOI analyzer 22, such as to provide metadata that can also include the time (e.g., time stamp data) corresponding to the time in which the measurements were made. The intracardiac SOI analyzer 22 can provide determined intracardiac electrical characteristics to the output generator 18 to create a corresponding three-dimensional map that is provided as part of the output data 20 for visualization. For example, the position data can be generated in real time and utilized by the output generator to dynamically update 3D map to graphically present the detected position of the device in real time.

As a further example, during a treatment procedure such as ablation, a user can usually visually monitor one or more of the intracardiac electrical characteristics determined by the intracardiac SOI analyzer 22 (e.g., provided in the output data 20) to monitor the output or change in one or more intracardiac electrical characteristics. In addition to computing intracardiac electrical characteristics for each of the plurality of sites in a given where the SOIs are measured, the intracardiac SOI analyzer 22 can also compute zone statistics (e.g., locally) by aggregating or performing other statistical methods (e.g., mean, standard deviation, variance, and the like) with respect to the intracardiac signal characteristics computed for each of sites within the given zone. For example, in response to ablating a given site within a zone, a user can ascertain changes at the site being ablated as well as one or more other sites within the zone by obtaining measurements at other sites within the zone concurrently with or following such ablation at such site. For instance the output generator can compare the one or more of computed intracardiac signal characteristics before treatment with corresponding intracardiac signal characteristics computed based on intracardiac data obtained during or after such treatment. Additionally or alternatively, the output generator 18 can be programmed to compare the zone data (e.g., specifying arrhythmia mechanisms, such as type and number) before treatment with corresponding intracardiac signal characteristics computed based on zone data derived from non-invasive data 12, which is computed from non-invasive measurements during or after such treatment. As mentioned, the treatment can include one or more components, such as including lifestyle changes, medicine, surgical procedures (e.g., ablation, pacing) and/or cardiac rehabilitation.

In the example of FIG. 1, the output generator 18 includes a prioritization engine 26 to determine a priority for the plurality of sites within one or more zones. The prioritization engine can be programmed to compute the priority based on the mechanism of distinct arrhythmogenic electrical activity determined by the arrhythmia electrical analyzer 16, based on the intracardiac signal characteristics determined for a plurality of sites within the respective zones or based on a combination (e.g., a weighted combination) thereof. The prioritization engine 26 can determine different types of priority such as including a zonal priority corresponding to a ranking or prioritization among a plurality of zones that have been identified by the arrhythmia mechanism analyzer 16. The prioritization engine 26 can determine zonal priority among the plurality of zones based upon the relative number of mechanisms of irregular activity that occur within each respective zones during one or more time intervals. For example, a zone containing a greater number of rotors and foci during a given time interval can be assigned a higher priority for treatment than zones containing a fewer numbers of rotors and foci. Additionally or alternatively the prioritization engine can determine zonal priority according to an indication of sustainability for mechanisms identified with each respective zone.

The prioritization engine 26 can also determine a local priority among the plurality of sites within each respective zone according to the plurality of sites where SOI measurements were obtained. For instance, the prioritization engine 26 can evaluate the plurality of different intracardiac signal characteristics for the sites within a given zone to determine a ranking or order for treatment among the sites within the given zone. As mentioned, in some examples, the intracardiac signal characteristics may include cycle length, cycle length variation, percentage of continuous activation and fractionation determined for respective SOIs.

The prioritization engine 26 can also assign different priority weightings to each the different types of intracardiac signal characteristics according to the particular mechanism(s) of distinct arrhythmogenic electrical activity (e.g., arrhythmias or dssynchrony) determined by the mechanism analyzer 16 for a given zone. In this way, the signal characteristics can be weighted and/or normalized to enable the prioritization engine 26 to determine the local priority within a given zone based upon the weighted signal characteristics for such zones. The weighting can be implemented by emphasizing and/or deemphasizing the contribution of different signal characteristics.

As one example, in response to determining the only mechanisms of an activity in a given zone include one or more rotors, the prioritization engine 26 can apply a greater priority weighting to the percentage of continuous activation characteristic that is computed relative to the other intracardiac signal characteristic determined for the given zone. In this way the percentage of continuous activation that is computed for each site in a given zone can contribute to a greater extent to the prioritization of each respective site within such zone that contains only rotors. Stated differently, other signal characteristics (e.g., cycle length characteristics and fractionation) will contribute less to the determination of priority by the prioritization engine 26 compared to percentage of activation.

As another example, in response to determining that the only mechanisms of irregular activity within a given zone include one or more foci, a greater (e.g., increased) priority weighting can be attributed to the cycle length characteristics, such as cycle length and/or cycle length variation, relative to other intracardiac signal characteristics that are determined for the given zones. In this way, when no rotors and one or more foci have been detected in a given zone, the cycle length characteristics can be emphasized as to contribute to a greater extent over other intracardiac signal characteristics in the determination of priority among the plurality of sites within the given zone.

In an example where a given zone contains multiple different types of arrhythmia mechanisms, a corresponding weighting that is proportional to the numbers of each respective type of mechanism within the given zone can be applied to the different intracardiac signal characteristics for use in determining a corresponding priority among the plurality of points. The resulting priority of the sites can be provided as part of the output data 20 which can be identified (e.g., graphics, text and/or color coding) in a three-dimensional map superimposed on the anatomical structure. A table or other listing of the sites in the order of priority can also be generated in the output data 20 for display to the user.

As disclosed herein, the system 10 can be utilized as part of an EP study or other form of procedure that can integrate non-invasive electrical data and intracardiac data to obtain information about a patient's anatomy, such as part of a treatment planning process. In other examples, the system 10 can be utilized as part of a treatment process in conjunction with applying treatment, such as directly to sites within the identified zones according to the priority that has been determined by the prioritization engine 26. Additionally, other forms of treatment can be utilized for directly or indirectly treating the patient, the results of which can be evaluated via the system 10.

Figure 2:
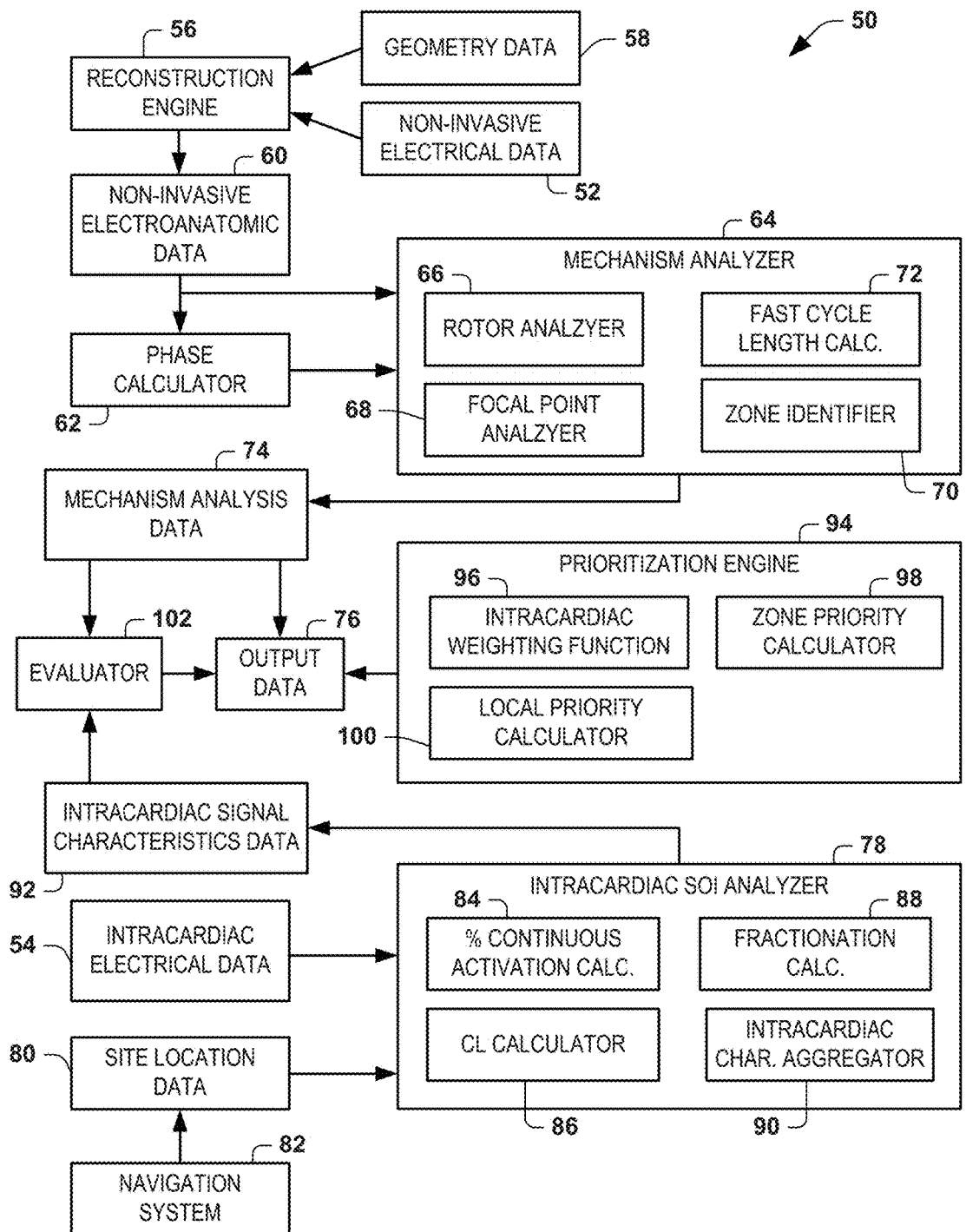
FIG. 2 depicts an example of a block diagram demonstrating a system for integrating invasive and noninvasive information.

FIG. 2 depicts another example of a system 50 to integrate invasive and non-invasive electrical information. The system 50 includes a non-invasive subsystem that is configured to process non-invasively acquired electrical data 52. The non-invasively acquired electrical data 52 can be employed to provide a global view of a region of interest of a desired anatomical structure of the patient such as to provide a beat-by-beat information across multiple chambers and, in some cases, the entire cardiac surface. Another subsystem can process intracardiac electrical data 54 such as can be stored memory based upon measurements made invasively for a plurality of points based on sensors positioned within a patient's body. While the intracardiac electrical data 54 can be based on invasively obtained measurements, such as via direct measurements and/or applying a transform to convert reconstructed electrical signals to approximate directly measured signals (e.g., transform derived from invasive and non-invasive measurements, as mentioned above), the system 50 does not require any particular source of information. Stated differently, the system 50 processes the data 54 and 52 that has been stored in memory and does not require any treatment or interaction with a patient to perform the functions and methods disclosed herein. Thus, the system 50 can be implemented as machine readable instructions stored in memory, which instructions and associated data can be accessed and executed by one or more processing units.

The system 50 can include a reconstruction engine 56 to process the non-invasive electrical data 52 in conjunction with geometry data 58 to provide corresponding non-invasive anatomic data 60 for an anatomic envelope such as a cardiac surface. As used herein, an envelope can correspond to an actual anatomic surface (e.g., the epicardial surface) or a virtual surface within a patient's body that is associated with the region of interest, namely a patient's heart. The geometry data 58 can be stored in memory based upon information obtained via an imaging system, such as magnetic resonance imaging (MRI), computed tomography (CT), xray or other system.

For example, the geometry data 58 can include information in a three-dimensional coordinate system that represents the spatial geometry of the anatomic region of interest (e.g., a patient's heart), the spatial location of the plurality of sensors that are utilized to measure the non-invasive electrical data 52 relative to the location of the heart and the location of the body surface on which the sensors have been positioned. A reconstruction engine 56 is configured to reconstruct electrical activity for a plurality of nodes spatially distributed over a cardiac envelope based on the geometry data 58 and the non-invasive electrical data 52 acquired over one or more time intervals. In some examples, the number of nodes can be greater than 1,000 or 2,000 or more depending upon the reconstruction process implemented by the reconstruction engine 56.

As a further example, the non-invasive electroanatomic data 60 can correspond to unipolar or bipolar electrograms at nodes spatially distributed over the cardiac envelope. In the example of FIG. 2, the system 50 also includes a phase calculator 62 to compute phase of the electrical signals (e.g., electrograms) that have been reconstructed onto nodes distributed over the cardiac envelope.

As an example, the geometric envelope can be represented as a mesh, including a plurality of nodes interconnected by edges to define the mesh. The phase calculator 62 can be programmed to convert each cycle of electrical signal into a periodic signal as a function of time. For example, the phase calculator 62 can assign each point in time in between the beginning and end of each cycle a phase value, such as between [−π and π] in an increasing manner. The phase calculator 62 can compute the phase information for several time intervals at various points in time to make the analysis robust in terms of temporal and spatial consistency. In some examples, the phase calculator 62 can provide corresponding phase data for each location (e.g., about 2000 or more points) on the cardiac envelope for one or more time intervals for which the electrical data has been acquired. Since the electrical signals can be measured and/or derived concurrently for an entire geometric region (e.g., over up to the entire heart surface), the computed phase data and resulting wave front likewise are spatially and temporally consistent across the geometric region of interest. In some examples, the phase data thus can correspond to phase across the entire surface of the patient's heart. In other examples, the phase data can correspond to one or more regions of interest which can include multiple chambers of a patient's heart for the same time intervals.

An example of how the calculator can determine phase based on electrical data 14 for a surface is disclosed in PCT Application No. PCT/US13/60851 filed Sep. 20, 2013, and entitled PHYSIOLOGICAL MAPPING FOR ARRHYTHMIA, which is incorporated herein by reference. Other approaches could also be utilized to determine phase, in other examples. In some examples, the non-invasive electrical data can correspond to real time data that is acquired over time. In other examples, the non-invasive electrical data that is acquired from the sensors attached to the patient's body surface prior to an EP procedure study or the like.

The system 50 includes an mechanism analyzer (e.g., corresponding to the analyzer 16 of FIG. 1) 64 programmed to identify one or more mechanisms of distinct arrhythmogenic electrical activity based on the reconstructed electrical signals, corresponding to the non-invasive electroanatomic data 60 and/or based on the phase data determined by the phase calculator 62. As mentioned above, the phase data and the electroanatomic data 60 can represent phase and electrograms, respectively, for each of the plurality of nodes distributed over the cardiac envelope.

The mechanism analyzer 64 can identify one or more zones within a region of interest of a cardiac envelope (e.g., a surface of a patient's heart) that contains one or more mechanisms of distinct arrhythmogenic electrical activity. In the example of FIG. 2, the mechanism analyzer 64 includes a rotor analyzer 66, a focal point analyzer 68, a zone identifier and a fast cycle length calculator 72. While three such methods are demonstrated in the example of FIG. 2 for detecting and characterizing arrhythmia mechanisms, the analyzer 64 can be extensible and user programmable to detect and identify other mechanisms.

For example, the analyzer 64 can also compute an indication of synchrony within a selected region or among multiple regions, such as can include inter-chamber synchrony (e.g., biatrial or biventricular) as well as intra-chamber synchrony for multiple regions with a given chamber. As one example, the analyzer 64 can compute one or more indexes to describe an indication of synchrony, such as a global index or a regional index, for one or more regions on the anatomical ROI (e.g., cardiac envelope) based on non-invasive electrical data, such as disclosed in the U.S. Patent Publication No. 2013/0245473, corresponding to U.S. patent application Ser. No. 13/882,912, which is incorporated herein by reference.

By way of example, the rotor analyzer 66 can be programmed to analyze the phase data stored in memory to detect and characterize rotor dynamics temporally and/or spatially for the cardiac envelope. For instance, the rotor analyzer 66 can identify locations on the geometric surface corresponding to one or more rotor core trajectories based on wave front data derived from the phase data. The rotor analyzer 66 can also detect one or more stable rotor cores and derive related information for one or more of the detected stable rotors. For example, the rotor analyzer 66 can compute statistics for stable rotors across the geometric surface over time and/or ascertain connectivity between rotors.

For example, the rotor analyzer 66 can group rotors into respective zones depending on the anatomical location where such rotors are detected on the cardiac envelope. Within a zone, rotors can be counted a few different ways. As one example, summing the total number of rotations in a given zone can be summed together to provide an indication of the number of rotors. Another example to quantify rotors in a spatial zone is a sustainability index (e.g., a ratio for a region or globally) over a defined time interval (e.g., a duration selected automatically or in response to a user input) as follows:

$$\text{Rotor Sustainability} = \frac{\sum \text{rotor rotations}}{\sum \text{rotor detections}} \qquad \text{Eq. 1}$$

For instance, zone 1 has 4 detections: 1.5, 1.5, 3, and 2 rotations. Zone 2 has 2 detections: 2.5, 3. First method yields 8 rotors in Zone 1 and 5.5 rotors Zone 2. The second example method (e.g., sustainability ratio) results in 2 (e.g., sum of all/# of detections from Eq. 1) for Zone 1, and 2.75 for Zone 2.

As a further example, the rotor analyzer 66 can compute a time-weighted average on the nodes along each trajectory and remove nodes that are further than a predetermined distance from a center (e.g., centroid) of the identified wave break point trajectory. After nodes that are further than the predetermined distance are removed, another average can be computed until all of the remaining points are within a predetermined distance (e.g., a radius) from the center of the remaining trajectory. The process can further be repeated until all of the remaining portions that are not within a predetermined distance of the center have been removed, until they are part of some sub trajectory.

As another example, the rotor analyzer 66 can implement a clustering algorithm to cluster wave break points, spatially and temporally, in a given rotor core trajectory based on the predetermined distance for clustering the rotor to determine the stable portions. Each stable rotor portion can define a respective rotor and the total number can be aggregated for a given zone (e.g., spatially and/or temporally) to provide the number of rotors that occur with such zone during the one or more time intervals. The resulting rotor information can be stored in mechanism analysis data 74, and utilized to generate a graphical visualization to present spatially and temporally consistent information in the one or more maps (e.g., presented according to a color scale or grayscale). An example of methods that can be implemented by the rotor analyzer 66 is disclosed in U.S. patent application Ser. No. 14/273,458, filed May 8, 2014, and entitled ANALYSIS AND DETECTION FOR ARRHYTHMIA DRIVERS, which is incorporated herein by reference.

The focal point analyzer 68 is configured to identify one or more focal points based upon the phase data computed for the nodes in the cardiac envelope. A focal point (referred to herein in the plural as foci) corresponds to one or more origins of electrical activity, such as an arrhythmias (e.g., atrial fibrillation, atrial tachycardia, ventricular fibrillation, ventricular tachycardia or the like). A focal point can thus refer to any point a location where an activation initiates and spreads out from such initial location to its surrounding tissue. By way of example, the focal point analyzer 68 can identify foci for a given geometric surface based on analysis spatial and temporal information related to activation and phase of signals for nodes across a geometrical surface. The analysis can include a comparison of a phase of node on the given geometric surface relative to the phase of nodes residing in a neighborhood (e.g., one or more layers of nodes) around the given node. The comparison can be made between the given node and its neighboring nodes over a time period sufficient to encompass a trigger event—corresponding to a focal point. For instance, neighbors of a focal point node have a later activation time, but are synchronized in phase with respect to each other. Scores can be assigned to each focal point. A corresponding focal point map can be generated based on the scores accumulated for each node across one or more time intervals. The phase data for the nodes can be provided by the phase calculator as mentioned above, and the activation times for such nodes can be determined for such nodes based on the electroanatomic data 60.

As another example, the focal point analyzer 68 can identify focal points for a given geometric surface by analyzing a set of one or more focal candidate nodes according to a spread of activation from an initial focal candidate node relative to surrounding nodes in a neighborhood (e.g., one or more layers) around the initial candidate node. For instance, the focal point analyzer 68 employs rules evaluate the spread of activation spatially and temporally to determine whether or not to classify the initial focal candidate node as a focal point. The resulting focal point data can also be stored in mechanism analysis data 74 and utilized to generate a graphical visualization to present spatially and temporally consistent information in the one or more maps (e.g., presented according to a color scale or grayscale).

By way of further example, from a mathematical definition, at a given time t, the focal point analyzer 68 can determine that a focal point occurs at a given node x if $$\phi_x(t) > \phi_{l,i}(t), \forall l=1 \ldots n, i \in N_l(x), \qquad \text{Eq. 2}$$

where: $\phi_x(t)$ is the phase value at vertex x at time t,
$\phi_{l,i}(t)$ is the phase value at the ith vertex in the lth layer of neighborhood,
n is an adjustable parameter to control number of layers, and
$N_l(x)$ is a set containing all vertices in the lth layer of neighborhood of vertex x, as demonstrated in the layered neighbor diagram of FIG. 2.

To make this process robust against noise, several layers (e.g., n=2 to n=4 or more) of neighbors around a given node can be utilized. A focal trigger typically will last at least a few milliseconds. Accordingly, the inequality above shall hold for a few consecutive samples across a time interval.

$$\phi_x(t) > \phi_{l,i}(t), \forall l=1 \ldots n, i \in N_l(x), t=1 \ldots m \qquad \text{Eq. 3}$$

where m is an adjustable parameter to control the minimum duration of this event to classify a vertex to be a focal (e.g., m=5 ms).

The phase comparison based on Eq. 3 can be performed at the time of activation for node X as well as for a post activation period of time following the activation time. The time period for which the comparison is evaluated following activation at X can be a fixed default time period or it may be user programmable. In some examples, a variable evaluation time period can be set to vary based on the number of layers being evaluated in the neighborhood of node X (e.g., a greater number of layers can employ a larger time period to accommodate for spread). As an example, the activation time for each node, including the given node X, can be determined based on a time derivative of the electrogram signal at X, such as may be the time of minimum slope for the electrogram at X or maximum absolute slope; although other activation time detection algorithms may be used.

To represent the focal detection result numerically, for each node detected as a focal point per Eq. 3 above, phase comparator can score a given node with 1, for multiple instances occurring at the same or different nodes, such that the focal point analysis module 14 can accumulate scores for each node. As a mathematical example, the focal point analysis module 14 can compare computed phases of neighboring signals to determine a score $F_x(t)$ for vertex x at a given sample time t, which can be represented as follows:

$$F_x(t) = \begin{cases} 1, & \text{if } \phi_x(k) > \phi_{l,i}(k), \forall l=1 \ldots n, i \in N_l(x), \\ & k=t+1, \ldots, t+m \\ 0, & \text{otherwise} \end{cases} \qquad \text{Eq. 4}$$

The focal point analysis module 14 can further calculate an aggregate score over time, such as can be represented as follows:

$$CF_x = \sum_t F_x(t) \qquad \text{Eq. 5}$$

As a further example, the focal point analyzer 68 can establish a variable scoring to be applied for each comparison. Thus, instead of scoring each comparison between a vertex node and a neighboring node to be 1 or 0, as mentioned above, comparisons between a vertex node and neighbors can vary as a function of distance between nodes being compared. The focal analysis can further determine other focal statistics, such as including but not limited to those disclosed in PCT Publication No. WO 2014/113555, corresponding to International application no. PCT/US2014/011825, filed Jan. 16, 2014, and entitled FOCAL POINT IDENTIFICATION AND MAPPING, which is incorporated herein by reference.

As yet another example, the focal point analyzer 68 can be programmed to characterize sustainability of focal drivers at a given anatomical location on a cardiac envelope based on the electroanatomic data. For example, the focal point analyzer 68 calculates the number of times (e.g., occurrences) that a focal source discharges from a given anatomical location, over a prescribed time interval (e.g., an AF interval). Therefore, over a given interval each foci location will have an associated focal discharge count. The average foci discharge count of all detected sources yields the global foci sustainability index. The average foci discharge occurrence of all detected locations, within a given anatomical region, yields the local foci sustainability index. such as follows.

$$\text{Foci Sustainability} = \frac{\sum \text{focal discharges}}{\sum \text{intervals where occurred}} \qquad \text{Eq. 6}$$

A fast cycle length calculator 72 can be programmed to compute regions of fast cycle length (e.g., cycle length acceleration) such as to identify bursting drivers based on the non-invasive electroanatomic data 60. For example, the cycle length calculator 72 can compute activation time as a function of the periodic nature of the reconstructed electrograms in the electroanatomic data 60 for nodes on the cardiac envelope. The cycle length can be detected over the duration of time between consecutive activation time occurs between each adjacent pairs of beats in the interval. The cycle length can be computed for each of the plurality of nodes for which the electrograms have been reconstructed on the cardiac envelope.

For example, the fast cycle length calculator 72 can compute the average cycle length for the plurality of reconstructed electrograms for nodes distributed across the cardiac envelope. If the average cycle length for the nodes during a time interval is sufficiently low (e.g., below a prescribed threshold, which can be user programmable), a fast cycle length node can be identified for each such node. In other examples, the average value of cycle length for the zone can be stored in memory and utilized for comparing a relative cycle length among each of the plurality of zones that have been identified by the zone identifier 70.

Additionally, as disclosed herein, the mechanism analyzer 64 can determine sustainability of a plurality of mechanism drivers (e.g., rotor and focal drivers focal discharge), and a total sustainability could be computed by aggregating normalized values of the indices computed for each such driver. For the example, where the mechanisms include rotor and focal drivers, Eqs. 1 and 6 can be combined to provide an aggregate sustainability, representing the degree of driver sustainability, in an anatomical location (local) or in a larger region (global), such as follows:

$$\text{Driver Sustainability} = \Sigma(\text{Rotor Sustainability} + \text{Foci Sustainability}) \qquad \text{Eq. 7}$$

The zone identifier 70 can be programmed to identify one or more zones based on one or a combination arrhythmia mechanisms determined by the rotor analyzer 66, focal point analyzer 68 and fast cycle length calculator 72, such as described above. In some examples, a given zone may be an identified spatial area on the cardiac envelope. In other examples, the zone can include spatial and temporal components for one or more mechanisms. As an example, the zone identifier 70 can employ a clustering algorithm to identify a spatial area across the cardiac envelope to group rotors, focal points and/or fast cycle length nodes within bounded regions that define each respective zone.

By way of example, each zones can be identified by any of following 1) user predefine regions from CT geometry, 2) mechanism overlaps grouped as 1 region until perimeter beyond a threshold X, 3) manual definition on map depending upon locations of detected mechanisms.

1) Following cardiac segmentation, user defines perimeter by drawing the zones on the cardiac envelope, each with unique anatomical name. Such drawing of the zones can be done before reconstruction, provided that cardiac mesh points are known.
2) Automatic zone definition can be determined based upon the spatial overlap of mechanisms (e.g., rotor drivers, focal point drivers or bursting drivers). A given zone would extend as far as there is overlap, until it reaches certain threshold. In this case, the automatic zone definition can split "oversize zone" in ½.
3) Post-inverse problem and rotor/foci detection, user can circle regions specific to that patient in response to a user input (e.g., via a drawing tool). Based on the encircled regions, the set of node points with in each region would be spatially registered as residing with the zones.

The arrhythmia mechanism analyzer 64 in turn can provide mechanism analysis data 74, which that can include an identification of the spatial region corresponding to each identified zone as well as statistics associated with the arrhythmia mechanisms that have been identified therein from non-invasive data. Such statistics, for example, can include an identification of the number of rotors that occur in a given zone during a given time interval, the number of focal points within a given zone during the given time interval as well as the cycle length for the respective zone in the given time interval. The mechanism analysis data 74 thus can be provided as output data 76 which can be in turn rendered as part of a graphical 3D map on a display or other form of output device. The mechanism analysis data 74 further can be stored in memory and utilized by other systems and methods disclosed herein.

The system 50 can also include an intracardiac SOI analyzer (e.g., corresponding to the analyzer 22 of FIG. 1) 78 to analyze intracardiac electrical data 54 which can be stored in memory. For example, the intracardiac electrical data 54 can be acquired for one or more anatomic sites during a measurement interval based upon electrical signals measured directly from one or more sensors such as on a probe, catheter or other measurement device. The intracardiac electrical data 54 can be combined with site location data 80 to provide an indication of the location for each of the sites at which the electrical activity was measured as provided by the intracardiac electrical data 54, which can be co-registered with the coordinate system as the non-invasive electroanatomic data 60. The site location data 80, for example, can be provided by a navigation system 82.

As one example, a probe catheter or other device can be positioned within a patient's body to measure electrical activity at a plurality of sites. As one example, each of the sites can correspond to positions within one or more zones that have been identified in the mechanism analysis data 74 (e.g., as determined by the zone identifier 72). In some examples, the site location data 80 can be utilized to provide a graphical representation for the location of the device being used to obtain the measurements that are stored as the intracardiac electrical data 54 to facilitate localization of the measurement device to a desired measurement site within an identified zone. Once the device is positioned within a given zone, measurement data for a signal of interest can be recorded and stored in the memory as the intracardiac electrical data 54 for a plurality of sites within the given zone. This measurement process can be repeated for any number of sites (e.g., four or more sites) within each identified zone.

The intracardiac signal characteristics can be computed by a plurality of signal characteristic calculators. In the example of FIG. 2, the calculators implemented by the SOI analyzer 78 include a percentage of continuous activation calculator 84, a cycle length characteristic calculator 86, a fractionation calculator 88, and an intracardiac characteristic aggregator function 90. Each of the calculations 84-90 can compute corresponding statistics for each of the sites that can be stored collectively as intracardiac signal characteristic data 92 for each respective zone.

As a further example, the percentage continuous activation calculator 84 can compute a percentage of continuous activation for each of the plurality of sites within the given zone. The percentage of continuous activation can be computed by calculating activation time based upon the measured electro activity such as activation corresponding to the derivative of the measured signal, signal peaks in the bipolar electrogram (determined via frequency or peak amplitude analysis as examples) (e.g., DV/DT). The percentage of the measurement time interval during which activation occurs (e.g., activation zones), can be stored as the percentage of continuous activation.

As an example, the percentage continuous activation calculator 84 identifies the active interval around each local activation detection. Based upon frequency and amplitude thresholding criteria, an active zone is defined as the zone surrounding an activated peak which meets the frequency and amplitude thresholding criteria. This segment of signal is the active portion. The continuous activation calculator 84 in turn computes the percentage of continuous activation as the ratio of active portion to passive portion (e.g., the remaining signal).

The cycle length calculator 86 can leverage the activation time that is computed by the calculator 84 (and/or calculator 72). For instance, each of the activation times determined over the measurement interval at a given measurement site can be evaluated to compute cycle length (e.g., cycle length determined as a time difference between activation times between consecutive beats). An average cycle length over the measurement interval thus can be calculated by averaging the cycle length values over such interval. The cycle length calculator 86 can also compute an indication of cycle length variation, such as corresponding to a standard deviation or standard error of the cycle length that was computed. Thus the cycle length calculator 86 can compute both a mean cycle length and a cycle length variation, which can be stored in the intracardiac signal characteristics data 92 as cycle length characteristics for each measurement site within each identified zone.

The fractionation calculator 88 can compute an indication of fractionation for each of the electrograms provided in the electrogram electrical data over a measurement interval. The fractionation can correspond to an average fractionation detected among corresponding beats that have been identified during the measurement interval for each of the plurality of sites. For example, the fractionation calculator can perform a signal analysis on the corresponding electrogram for the measurement interval to detect a frequency of instances of alternating increasing and decreasing potential in the measured SOI. For example, the fractionation calculator can take the time derivative (dv/dt) for the SOI to detect changes in slope (e.g., between positive and negative values) in the signals during the measurement interval. The amount of fractionation during the measurement interval can be normalized and stored as a fractionation value (e.g., a fractionation index) in the intracardiac signal characteristic data 92.

The intracardiac characteristic aggregator 90 can aggregate the computed intracardiac characteristics (e.g., cycle length, cycle length variation, percentage continuous activation, fractionation, slope steepness) within a given zone such as by averaging the computed characteristics for sites within a given zone over time to provide an average value of the intracardiac characteristics for each respective zone (e.g., identified by zone identifier 70). The aggregate characteristics for each zone can also be stored as part of the intracardiac signal characteristic data 92.

The system 50 can also include a prioritization engine 94 to determine priority for zones and/or sites within each of the zones based on the mechanism analysis data 72 and the intracardiac signal characteristic data 92. The prioritization engine 94 can include a zone priority calculator 98 to determine a priority among the plurality of different zones that have been identified by zone identifier 72 of the arrhythmia analyzer 64. For example, there can be any number of spatial zones that have been identified across the surface of interest according to the non-invasive electrical data 52.

As one example, the zone priority calculator 98 can compute the zone priority based on the mechanism analysis data 74. For example the zone priority calculator can set the zonal priority according to the total number of arrhythmia mechanism that have been identified to occur within each respective zone during a given measurement interval. Thus, the zone with the highest number of arrhythmia mechanisms can be assigned a higher priority value relative to zones having fewer numbers. Additionally or alternatively, the zone priority calculator 98 can determine the zonal priority among the plurality of zones that have been identified based on comparing the average of the intracardiac signal characteristics that have been determined for each respective zone (e.g, by the intracardiac characteristic aggregator 90). As yet another example, the zone priority calculator 98 can determine the zonal priority among the plurality of zones that have been identified based on a combination of the number of mechanisms and the average of the intracardiac signal characteristics. Such combined priority is computed for each zone as a weighted average between mechanism occurrence and SOI statistics to determine zone priority among the zones. The zonal priority thus can be stored as part of the output data 76 and utilized by a practitioner to determine a treatment priority among the zones that have been identified as containing arrhythmia mechanism. Additionally or alternatively, the priority can provide a ranking for locations requiring further analysis (e.g., based on measurements for an increased number of sites).

The prioritization engine 94 can also include a local priority calculator 100 that can be programmed to compute a local priority among the plurality of sites within each zone for which intracardiac electrical data 54 has been acquired. The local priority calculator 100 can determine the local priority among the sites for each respective zone by evaluating the intracardiac signal characteristics for the sites within each respective zone. The local priority calculator 100 can be programmed to selectively employ one or more of the intracardiac signal characteristics (stored as data 92) for a given zone based upon the arrhythmia mechanisms that have an identified for the zone as provided by the mechanism analysis data 74.

As a further example, the prioritization engine 94 can include an intracardiac weighting function 96 to assign different priority weighting to two or more of the different intracardiac signal characteristics that have been computed for the sites within a given zone. The weighting function 96 can assign the different weightings according to the mechanism(s) of distinct arrhythmogenic electrical activity that have been identified for each respective zone. As a result, the intracardiac signal characteristics can be selectively weighted to provided corresponding weighted signal characteristics according to the weighting that is applied by the weighting function 96. When such weighting is applied, the local priority calculator 100 can determine the local priority for the plurality of sites within the given zone based on the weighted signal characteristics for the given zone. As mentioned, the weighting can depend on the number and type of mechanisms that have been identified for each respective zone. Thus the intracardiac weighting function 96 can apply different weighting to different zones depending on the types and/or numbers that have been identified in each respective zones.

As one example, in response to determining that the only arrhythmia mechanisms in a given zone include one or more rotors, the intracardiac weighting function 96 can assign a greater priority weighting to the percentage of continuous activation characteristic relative to the other intracardiac signal characteristics that have been determined. In this way, the contribution of the continuous activation value is emphasized in determining the priority among the plurality of sites when only rotors or majority rotors are identified in a given zone.

In another example, in response to determining that the only arrhythmia mechanisms in a given zone include one or more focal points (foci), the intracardiac weighting function 96 can assign an increased priority weighting to a cycle length characteristics, including one or both of the cycle length or cycle length variation. In this way, when only foci or majority foci have been identified in a given zone, one or more cycle length characteristics (e.g., computed by the cycle length calculator) can be emphasized relative to the other intracardiac signal characteristics that have been determined by the SOI analyzer 78.

When the mechanism analysis data 74 for a given zone indicates that both rotor and foci have been identified in the given zone, the intracardiac weighting function 96 can weight different ones of the intracardiac calculator functions 84-90 proportionally to the number of each types of mechanisms of irregular activity that have been identified with a given zone. The particular weighting values assigned by the weighting function 96 can depend on a variety of circumstances specific to the patient, the type of measurement device utilized to acquire the intracardiac data 54 as well as other detected cardiac information based on one or both of the non-invasive electrical data and/or the intracardiac data 54. The prioritization engine 94 thus can provide the output data 76 to include an indication of zonal priority, such as mentioned above, as well as an indication of local priority of the sites for SOIs within each respective zone. Each priority that is determined can be graphically represented on a three-dimensional map of patient anatomy. Additionally or alternatively, the output data 76 can be employed to generate a report or list of the determined priority order for sites in each respective zone, such as can be presented in conjunction with the three-dimensional map. As an example, the priority can specify which sites contribute most to the identified arrhythmia mechanisms. Thus, the site priority within a given zone can provide a recommended treatment order for each of the sites in the given zone.

The system 50 can also include an evaluator 102 to evaluate changes that occur over time in the mechanism analysis data, in the intracardiac signal characteristics data or a combination thereof. For example, the evaluator 102 can be programmed to compare one or both of the mechanism analysis data 74 that identifies mechanisms over a corresponding time interval and the intracardiac signal characteristic data 92 that it includes an indication of one or more intracardiac signal characteristics determined for corresponding measurement intervals. Additionally, the evaluator 102 can also be programmed to evaluate changes in the non-invasive electroanatomic data 60 that is reconstructed from different time intervals for a given patient as well as information derived from such data. As yet another example, the evaluator can evaluate changes in the intracardiac electrical data measured from approximately the same sites over time.

By way of example, the mechanism analysis data 74 utilized by the evaluator 102 can correspond to data determined based on non-invasive electrical data 52 that was obtained prior to treatment of the patient as well as non-invasive electrical data that was obtained subsequent to or during treatment of the patient. The treatment can include application therapy directly to the heart, such as ablation, (e.g., radio frequency ablation, cryoablation, chemical ablation or surgical ablation) or application of electrical stimulus (e.g., pacing) or chemical stimulus to the heart. In other examples, the treatment can be indirectly administered, such as by chemicals, pharmaceuticals or other forms of cardiac treatment (e.g., exercise or lifestyle changes) administered to or by the patient. The evaluator 102 thus can compare the pre-treatment mechanism analysis data 74 with like data from one or more other different time periods, including intra- and post-treatment mechanism analysis data, in each of the zones. For example, the evaluator can determine improvement at the selected site residing in the given zone based on comparing an indication of synchrony across atria or regions of interest near to the given zone identified prior to applying the therapy with respect to synchrony across the atria or the regions of interest near to the given zone identified following the applying the treatment to the selected site. In response, the evaluator 102 can provide output data 76 specifying changes in one or more mechanisms distinct arrhythmogenic electrical activity for each respective zone and, in some cases identify new mechanisms, which may be attributable to such treatment. Since the mechanism analysis data is based on non-invasive data, the post-treatment non-invasive data 52 and 60 and corresponding mechanism analysis data can be obtained without having to perform an invasive EP study.

By way of further example, the intracardiac characteristic data 92 likewise can include data determined from intracardiac electrical data 54 obtained at multiple different stages, such as including pre-treatment stage prior to treatment of the patient, as well as data obtained during and/or after treatment, which may depend on the type of treatment such as mentioned above. The evaluator 102 can compare intracardiac signal characteristics data 92 for one or more sites (e.g., can be all or a subset of sites selected in response to a user input) with corresponding intracardiac data measured at different measurement time intervals for the same or approximately the same sites (e.g., localized to within about +/−5% of the original site). For example, the evaluator 102 can compare a first set of intracardiac signal characteristic data, such as pre-treatment data, at one or more selected sites with corresponding data from one or more other different time periods, including intra- and post-treatment data and generate comparison output data 76 specifying changes in each of the intracardiac characteristics. Additionally, a user can select which of the intracardiac characteristics to evaluate for changes in response to a user input.

The results of the comparison, which may include a calculated difference between the pre-treatment data and intra-treatment data for the pre and post treatment data, can also be stored in memory as the output data 76. The result of the comparison by the evaluator in the output data 76 further can be output to a display or other output device. In a particular example where the comparison includes pre-treatment and intra-treatment data, associated output data 76 (e.g., mechanism analysis data 74, intracardiac signal characteristic data 92 and data generated by evaluator 102) can be updated dynamically in response to the updated data 52 and 54 that is obtained (e.g., in real time) during the procedure. In this way, the output data 76 can provide dynamic feedback to the user demonstrating improvements, such as can include a reduction in the number of mechanisms of distinct arrhythmogenic electrical activity as well as changes in one or more of the intracardiac characteristics.

In some examples, it is understood that updates and changes that occur intraoperatively in response to treatment may include changes increased number or new mechanisms of arrhythmia that can be generated in response to treatment. Since the mechanism analysis data derived from reconstructed electrograms can identify mechanisms across the entire cardiac envelope concurrently, the mechanism analysis data 74 can identify changes across the entire cardiac surface in response to direct treatment in a localized part (e.g., a given zone) of the heart. For example, a treatment in a zone within the left atrium could result in a new zone being identified in the same zone or a different zone in response to such treatment. The system 50 thus can analyze any such new zone, including by the analyzers 64 and 78 and by the prioritization engine 94, to provide corresponding output data that can be presented to the user to provide additional guidance associated with the treatment procedure. Additionally, the system 50 has the ability to re-prioritize all zones based on the mechanisms that that exist at during one or more time intervals, including in newly appearing zones that manifest during and/or after treatment.

As a further example, the evaluator 102 can be programmed to generate the output data 76 with information to indicate whether or not a given treatment site has been sufficiently treated. As an example, the evaluator 102 can be programmed to determine that one or more intracardiac signal characteristics value for a given site have changed sufficiently relative to a predetermined threshold. The evaluator 102 can also be programmed to determine that the arrhythmia mechanisms in a given zone have reduced sufficiently (e.g., to zero or no mechanisms in the zone) which can also be utilized to specify that treatment can be terminated for a given zone. The indication can be automatic and graphically indicated (e.g., change in color or other graphical indicia) or audibly indicated to the user via a speaker, for example. In other examples, the number of mechanisms can be displayed on a display or other output device, and the user can terminate the treatment in response to determining (e.g., subjectively) that the number of mechanisms and/or intracardiac signal characteristics for a given zone and/or site meet expected parameters. Additionally, or alternatively, if the user perceives that no further changes occur in response to more treatment (e.g., ablation) at a given site, this can be an indication of a treatment endpoint for the given site.

Figure 3:
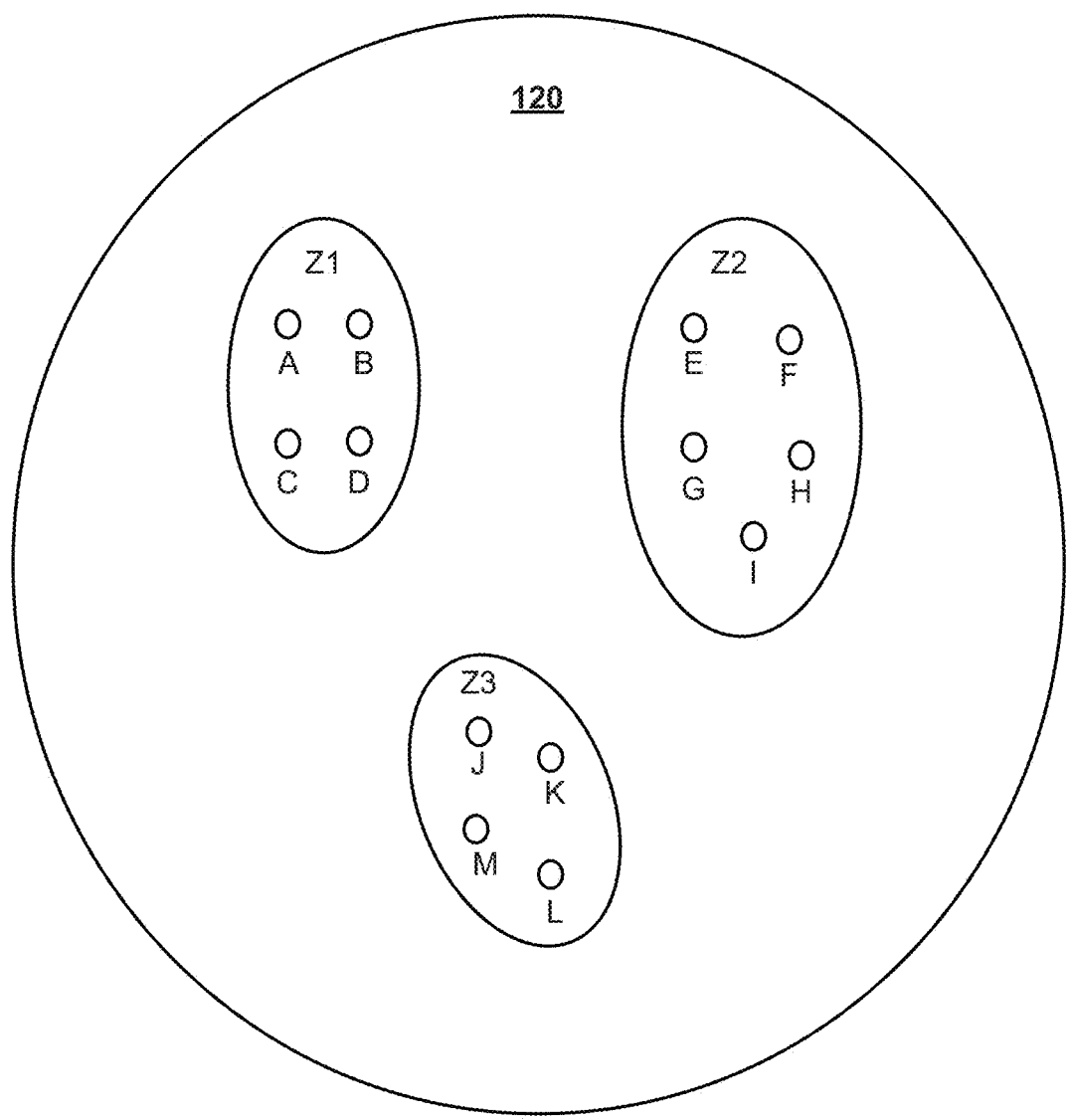
FIG. 3 depicts a schematic example of a heart that includes a plurality of zones including mechanisms of electrical irregularity.

As a further example, FIG. 3 depicts a simplified example of a patient's heart 120 and a plurality of zones demonstrated at Z1, Z2, and Z3. The heart and zones, for example, can be a three-dimensional map on an interactive graphical representation of a patient anatomy, such as a three-dimensional model of a heart. The heart 120 can correspond to a generic model of a heart, to a model generated from patient's anatomical data or a graphical model derived from a combination of patient geometry data and a generic model.

As demonstrated in the example of FIG. 3, each of the zones includes a plurality of sites corresponding to intracardiac sites. As disclosed herein, corresponding intracardiac electrical data can be measured invasively at each of the sites during respective measurement intervals. In some examples, after invasive measurements have been made at the sites within one or more zones, a transformation can be generated to transform non-invasively electroanatomic data spatially aligned with the localized sites into corresponding intracardiac data to provide a surrogate that simulates the invasive measurements. The intracardiac electrical data associated with respective sites can be stored in memory (e.g., as intracardiac electrical data 54). Similar transformations can be implemented with respect to other non-invasive electrical data.

In the example of FIG. 3, it is assumed that non-invasive electrical data has been utilized to construct non-invasive electrical anatomic data across the cardiac region of interest such as disclosed herein. Additionally, it is presumed at this stage that each of the zones Z1, Z2, and Z3 have been identified based upon analysis of arrhythmia mechanisms (e.g., by analyzer 64 or 14) and intracardiac electrical data has been obtained for a plurality of sites in each of the respective zones. For example, intracardiac data has be obtained for sites A, B, C and D contained in zone Z1. In zone Z2, intracardiac data has be obtained for sites E, F, G, H and I. Similarly, in zone Z3, intracardiac data has be obtained for sites J, K, L and M. With corresponding intracardiac electrical data (data 92 of FIG. 1) stored in memory for each of the sites A-M, corresponding intracardiac signal characteristics can be computed for each of the respective sites, such as disclosed herein.

Figure 13A:
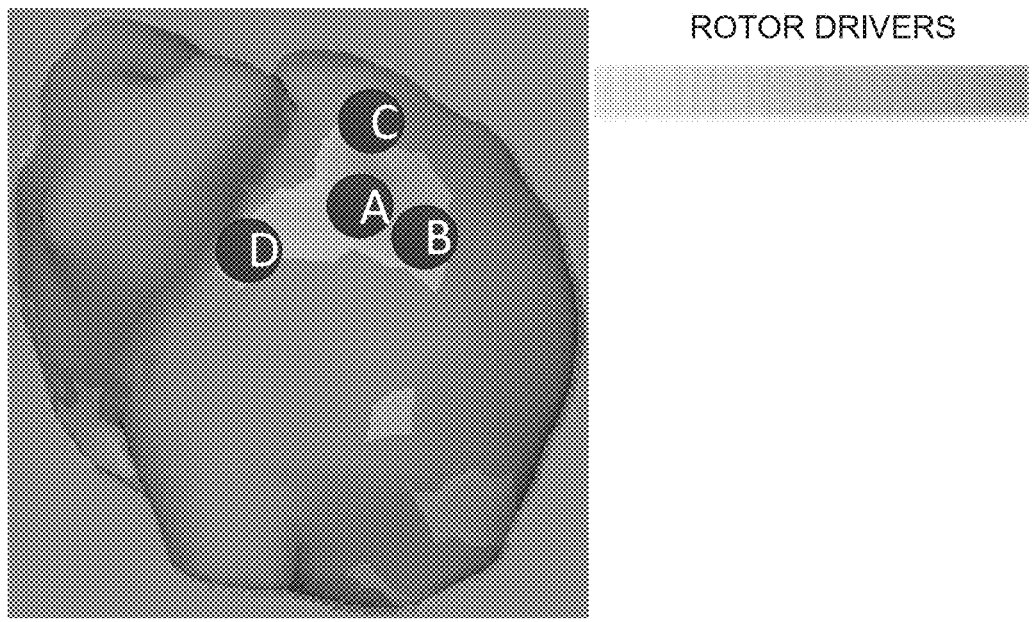
FIGS. 13A and 13B depict examples of graphical maps demonstrating signals of interest for a spatial zone containing rotors.
Figure 13B:
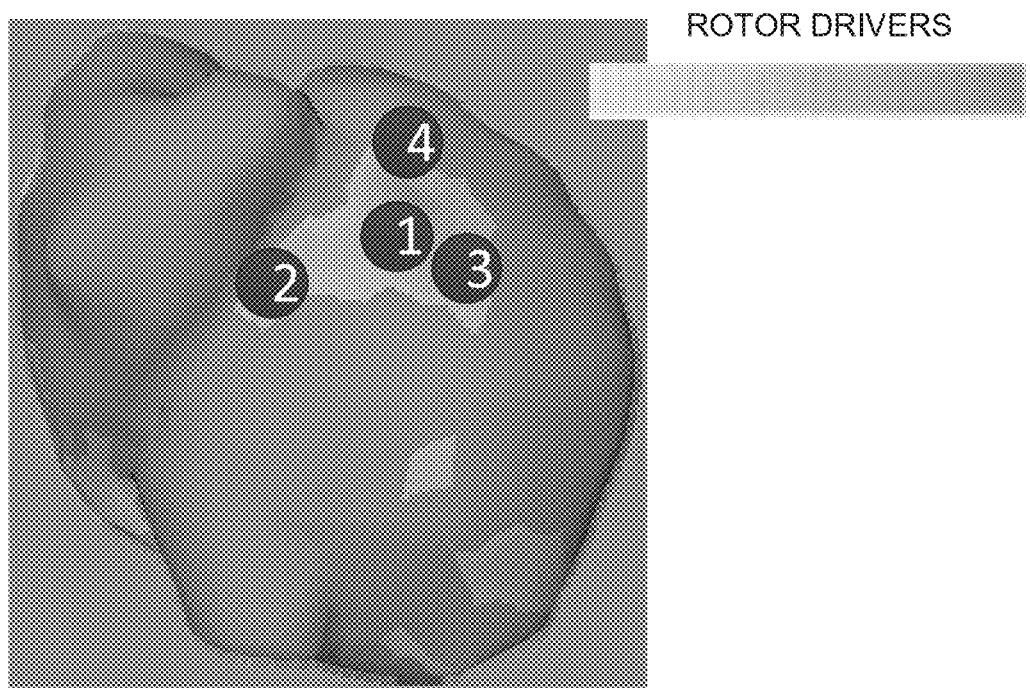

In the following example, it is assumed that at least initially zone Z1 contains six rotors and no foci, Z2 contains seven foci and no rotors and Z3 contains three rotors and two foci. The number and other characteristics of the mechanisms of distinct arrhythmogenic electrical activity can be determined (e.g., by mechanism analyzer 16 or 72) to provide mechanism analysis data, as disclosed herein. The following Table 1 includes examples of intracardiac signal characteristics that can be computed (e.g., by intracardiac SOI analyzer 22 or 78) for sites A, B, C and D in a given zone. FIG. 13A demonstrates a 3D graphical map of a heart showing a given zone with the sites labeled A, B, C and D for the given zone. The priority listed in Table 1 assumes that the zone includes 6 rotors, no foci and no burst drivers and corresponding weighting has been applied according to identified rotor drivers to provide a corresponding order of treatment priority demonstrated in table 1. FIG. 13B demonstrates a 3D graphical map of a heart showing a given zone with the sites labeled according to the determined weighted priority shown in Table 1.

TABLE 1

ZONE WITH 13 ROTORS (ZONE INDEX = 13)

| SITE | % CA | CL | CL VAR | FRAC | PRIORITY |
|---|---|---|---|---|---|
| A | 80% | 150 | 75 | 4.3 | 1 |
| B | 25% | 100 | 25 | 2.3 | 3 |
| C | 30% | 200 | 25 | 2.1 | 4 |
| D | 40% | 150 | 30 | 2.4 | 2 |
| Z1 AVE. | 44% | 150 | 39 | 2.8 | |

Figure 14A:
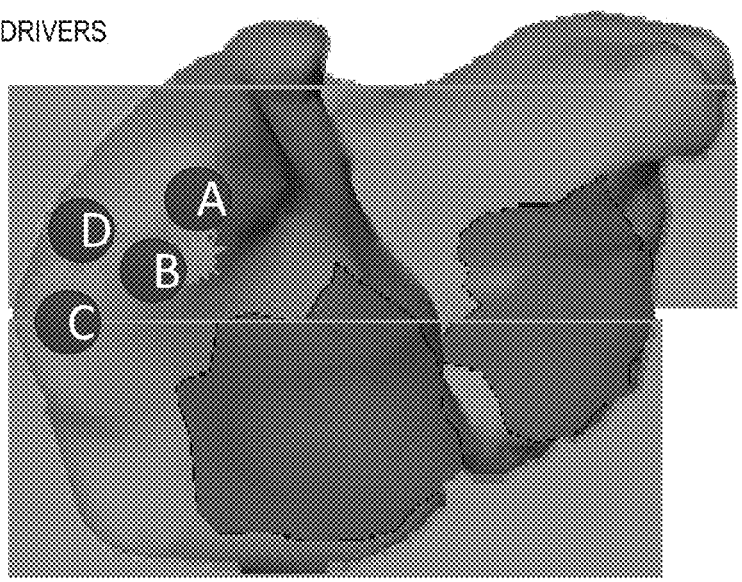
FIGS. 14A and 14B depict examples of graphical maps demonstrating signals of interest for a spatial zone containing foci.
Figure 14B:
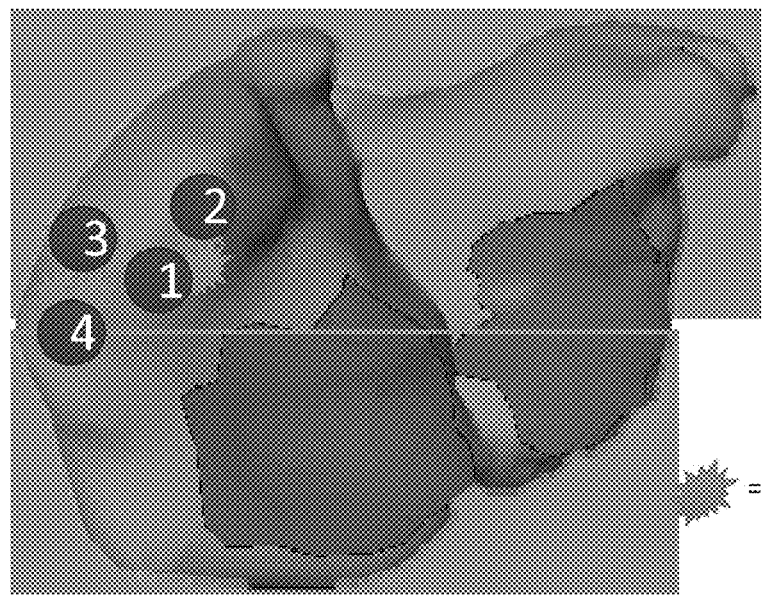

In the following table 2, for simplification of explanation, it is assumed that the same intracardiac characteristic values have been computed for sites A, B, C and D as in the example of Table 1, but for a different zone. In the example of Table 2, the priority weighting is applied assuming no rotors, 15 focal drivers and no burst drivers to provide the resulting priority order among the sites. FIG. 14A demonstrates a 3D graphical map of a heart showing the given zone with the sites labeled A, B, C and D for such zone. FIG. 14B demonstrates a 3D graphical map of a heart showing a given zone with the sites labeled according to the determined weighted priority shown in Table 2.

TABLE 2

ZONE WITH 15 FOCI (ZONE INDEX = 15)

| SITE | % CA | CL | CL VAR | FRAC | PRIORITY |
|---|---|---|---|---|---|
| E | 80% | 150 | 75 | 4.3 | 2 |
| F | 25% | 100 | 25 | 2.3 | 1 |
| G | 30% | 200 | 25 | 2.1 | 4 |
| H | 40% | 150 | 30 | 2.4 | 3 |
| Z2 AVE. | 80% | 150 | 75 | 4.3 | |

In the following table 3, for simplification of explanation, it is assumed that the same intracardiac characteristic values have been computed, but the priority weighting is applied assuming 9 rotors and 8 focal drivers and 2 burst drivers (See, e.g., Z3 in FIG. 15).

TABLE 3

ZONE WITH 9 ROTORS AND 8 FOCI and 2 BURST (ZONE INDEX = 19)

| SITE | % CA | CL | CL VAR | FRAC | PRIORITY |
|---|---|---|---|---|---|
| J | 80% | 150 | 75 | 4.3 | 1 |
| K | 25% | 100 | 25 | 2.3 | 2 |
| L | 30% | 200 | 25 | 2.1 | 4 |
| M | 40% | 150 | 30 | 2.4 | 3 |
| Z3 AVE. | 44% | 150 | 39 | 2.8 | |

In the examples of Tables 1-3, each of the intracardiac signal characteristics that have been computed for the respective sites. As disclosed herein, each cardiac weighting function can be applied to various intracardiac characteristics to determine a corresponding priority order according to the arrhythmia mechanisms detected for a given zone, such as indicated by the far right column in each table.

The information presented in Tables 1-3 can similarly be provided in an output display, such as in a separate window adjacent to a three-dimensional map of the patient's anatomy demonstrating electrical information that can be generated based on both non-invasive electrical data as well as intracardiac electrical data measured invasively. As an example, FIGS. 13-15 depict examples of 3D graphical maps of a heart surface showing signals of interest for respective measurement sites (A, B, C, D) contained within respective zones. As mentioned above, FIG. 13A demonstrates a graphical map of a zone that contains a plurality of rotors, where the characteristics of the identified rotors are indicated by an associated color coding scale. While the zone includes four sites for measurements of corresponding SOIs, this or any other zone may include any number of sites, such as can vary according to the user preferences or configuration of mapping catheter. In FIG. 13B the SOIs have been assigned a priority based on applying the priority weighting to the intracardiac signal characteristics determined for the zone (e.g., by SOI calculator 22 or 78). FIGS. 14A and 14B are similar to FIGS. 13A and 13B, respectively, but generated for zones graphical map of a zone that contains a plurality of focal drivers, where the characteristics of the identified focal drivers are indicated by an associated color coded star-like graphical feature.

Figure 15:
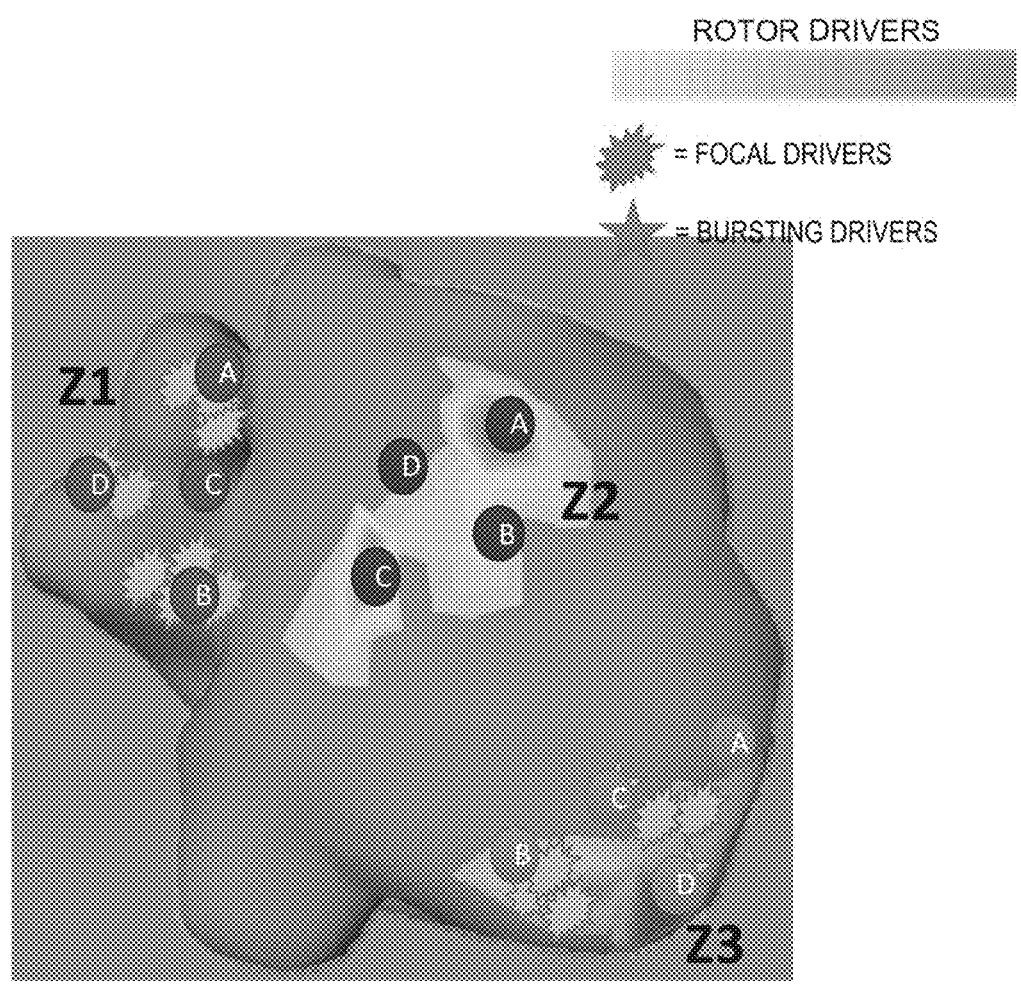
FIG. 15 depicts an example of a graphical map demonstrating a plurality of zones containing multiple arrhythmia mechanisms.

FIG. 15 depicts an example of a graphical map demonstrating a plurality of zones (e.g., three zones) containing multiple arrhythmia mechanisms. The types of mechanisms are indicated by a corresponding scale, such as demonstrated. In the example of FIG. 15, there are three zones Z1, Z2 and Z3 where zone Z1 contains 15 focal drivers (e.g., providing a zone index of 15), zone Z2 contains 13 rotors (providing a zone index of 13) and zone Z3 contains 9 rotors, 8 focal and 2 burst drivers (e.g., providing a zone index of 19). The indexes shown the foregoing, are demonstrated as a summation of driver activity, as one example. In other examples, where a region or zone includes multiple types of drivers and/or different strengths of drivers, the indexes can be calculated by applying a weighting criteria to these drivers.

Intracardiac characteristics for each of the zones can be determined from intracardiac signals of interest in each zone, such as disclosed herein. As also disclosed herein, the priority among the driver zones can be determined based on driver zone index derived from non-invasive electrocardiographic data (e.g, driver count, sustainability, or a combination thereof), based on an individual SOI index for each zone (e.g., weighted calculation across all parameters for a given SOI) calculated from invasive data or both invasive and non-invasive data, cumulative SOI index (e.g., weighted calculation across all averaged parameter values for a given driver zone) or based on a weighted average of driver zone index and the SOI index or indices.

It is to be understood that tables (or other forms of display) can be generated for any number of sites and zones that can be identified by integrating invasively acquired and non-invasively acquired information. Moreover, information can be obtained for different time intervals, such as static information obtained for a pretreatment time interval (e.g., to establish a baseline) and for a time interval after or during treatment, and be concurrently displayed. The corresponding data for the same locations, but for different time intervals, thus can be compared as disclosed herein (e.g., by evaluator 102 of FIG. 2) to provide additional guidance to a user or other individual performing a procedure or reviewing the results of a procedure.

Figure 4:
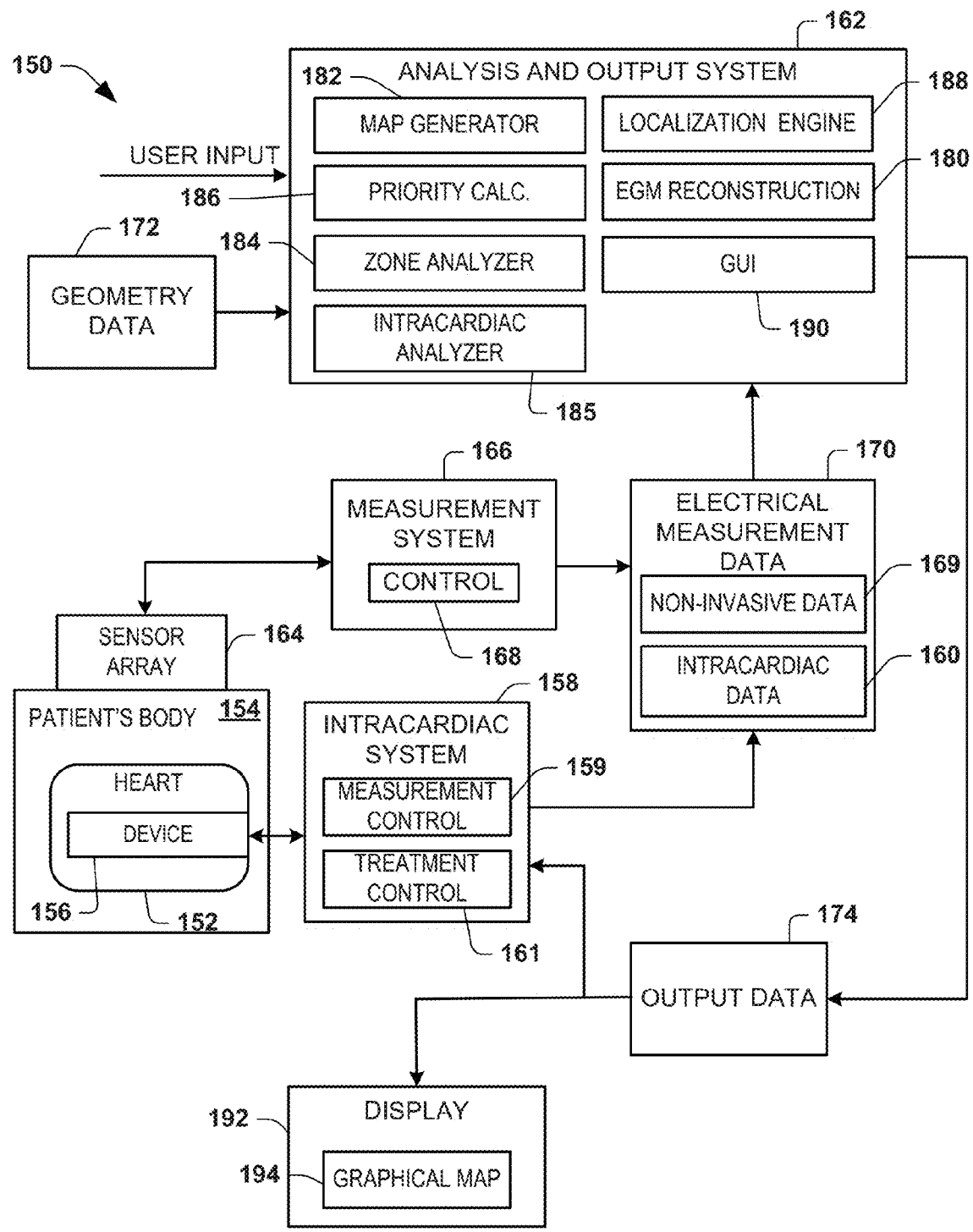
FIG. 4 depicts an example of a system that can be utilized for analysis and treatment of cardiac disease or disorder.

FIG. 4 depicts an example of a system 150 that can be utilized for performing diagnostics and/or treatment of a patient. In some examples, the system 150 can be implemented to generate corresponding graphical outputs for signals and/or graphical maps for a patient's heart 152 in real time as part of a diagnostic procedure (e.g., monitoring of signals during an electrophysiology study) to help assess the electrical activity for the patient's heart. Additionally or alternatively, the system 150 can be utilized as part of a treatment procedure, such as to help a physician determine parameters for delivering a therapy (e.g., delivery location, amount and type of therapy) and provide a visualization to facilitate determining when to end the procedure.

For example, an invasive device 156, such as a EP catheter, having one or more electrodes affixed thereto can be inserted into a patient's body 154. The electrode can contact or not contact the patient's heart 152, endocardially or epicardially, such as for measuring electrical activity at one or more sites. Those skilled in the art will understand and appreciate various type and configurations of devices 156, which can vary depending on the type of treatment and the procedure.

The placement of the device 156 can be guided based on position information determined via a localization engine 188, which can operate to localize the device 156. The guidance can be automated, semi-automated or be manually implemented based on information provided. The localization engine 188 can localize the device 156 and provide coordinates for the device and its electrodes. The localization engine can be implemented as part of an analysis and output system 162 or it can be a separate system that provides location data for the device and electrodes. Where a separate navigation system (e.g., a standalone system or integrated into the intracardiac system 158) is utilized to provide position data for the device 156, the navigation system can in turn provide location or position data to the analysis and output system, which can be stored in memory and co-registered with the geometry data 172 for the patient.

Examples of navigation systems commercially available include the CARTO XP EP navigation system (commercially available from Biosense-Webster) and the ENSITE NAVX visualization and navigation technology (commercially available from St. Jude Medical); although other navigations systems could be used to provide the position data for the device and associated electrodes. Another example of a navigation system that can be utilized to localize the position of the device 156 is disclosed in U.S. Provisional Patent Application No. 62/043,565, filed Aug. 29, 2014, and entitled LOCALIZATION AND TRACKING OF AN OBJECT, which is incorporated herein by reference. For example, the device 156 can include one or more electrodes disposed thereon at predetermined locations with respect to the device. Each such electrode can be positioned with respect to the heart via the device 156 and its location in a three-dimensional coordinate system can be determined by the localization engine 188 according to the type of navigation system. The sensors thus can sense electrical activity corresponding to each applied signal. The sensors can also sense other electrical signals, such as corresponding to real-time electrograms for the patient's heart.

The invasive measurement system 158 can include a measurement control 159 configured to process (electrically) and control the capture of the measured signals as to provide corresponding intracardiac data 160. The system 158 can also include a treatment control 161 to control application of treatment via the device 156, such as disclosed herein.

By way of example, the device 156 can apply the signal as to deliver a specific treatment, such as ablation, a pacing signal or to deliver another therapy (e.g., providing electrical therapy, or controlling delivery of chemical therapy, sound wave therapy, or any combination thereof). For instance, the device 156 can include one or more electrodes located at a tip of an ablation catheter, such as for applying RF energy for ablating the heart, in response to electrical signals supplied by the system 158. Other types of treatment can also be delivered via the intracardiac system 158 and the device 156 that is positioned within the body. The therapy delivery means can be on the same catheter or a different catheter probe than is used for sensing electrical activity via measurement control.

As a further example, the intracardiac system 158 can be located external to the patient's body 154 and be configured to control therapy that is being delivered by the device 156. For instance, the system 158 can also control electrical signals provided via a conductive link electrically connected between the delivery device (e.g., one or more electrodes) 156 and the system 158. The treatment control 161 can control parameters of the signals supplied to the device 156 (e.g., current, voltage, repetition rate, trigger delay, sensing trigger amplitude) for delivering treatment (e.g., ablation or stimulation) via the electrode(s) on the invasive device 156 to one or more location on or inside the heart 152. The treatment control 161 can set the therapy parameters and apply electrical or other treatment based on automatic, manual (e.g., user input) or a combination of automatic and manual (e.g., semiautomatic) controls. One or more sensors (not shown but could be part of the device) can also communicate sensor information back to the system 158. The location where such therapy is applied can also be determined (e.g., by localization engine 188 or in response to a user input), such as disclosed herein.

As one example, the position of the device 156 relative to the heart 152 can be determined by the localization engine 188, which can be tracked intraoperatively via an output system 162 when implemented during a procedure. The location of the device 156 and the treatment parameters thus can be combined to help control therapy as well as to record the location where the therapy is applied. The localization can also be performed based on previously stored data separately from a procedure. Additionally, the application of therapy (e.g, manually in response to a user input or automatically provided) can cause a timestamp or other time identifier to be tagged (e.g., as metadata) to the measurement data to identify when the therapy is applied and trigger localization to identify the location where the therapy is applied via the device 156. Other metadata describing the treatment (e.g., type, delivery parameters etc.) can also be stored in memory with the measurement data.

Before, during and/or after delivering treatment (e.g., via the system 158), the non-invasive measurement system 166 and/or measurement control 159 of system 158 can be utilized to acquire electrophysiology information for the patient. The analysis and output system 162 can implement methods programmed to identify one or more distinct arrhythmogenic electrical activity as well as intracardiac signal characteristics for sites within the identified zones, such as disclosed herein. In the example of FIG. 4, a sensor array 164 includes a plurality of sensors that can be utilized non-invasively for recording patient electrical activity. As one example, the sensor array 164 can correspond to a high-density arrangement of body surface sensors that are distributed over a portion of the patient's torso for measuring electrical activity associated with the patient's heart (e.g., as part of an electrocardiographic mapping procedure).

An example of a non-invasive sensor array 164 that can be used is shown and described in International Application No. PCT/US2009/063803, filed 10 Nov. 2009, which is incorporated herein by reference. Other arrangements and numbers of sensors can be used as the sensor array 164. As an example, the array can be a reduced set of sensors, which does not cover the patient's entire torso and is designed for measuring electrical activity for a particular purpose (e.g., an arrangement of electrodes specially designed for analyzing AF and/or VF) and/or for monitoring one or more predetermined spatial regions of the heart 152.

As mentioned, one or more sensor electrodes may also be located on the device 156 that is inserted into the patient's body. Such sensors can be utilized in conjunction with the non-invasive sensors in the array 164 for mapping electrical activity for an endocardial surface, such as the wall of a heart chamber, as well as for an epicardial envelope. The measurement system 166 can include appropriate controls and signal processing circuitry 168 for providing corresponding non-invasive electrical measurement data 169, which can be stored as part of the electrical measurement data 170 with the intracardiac electrical data 160. The measurement data 170 can include analog and/or digital information. The system 150 can also employ geometry data (e.g., corresponding to geometry data 58) 172 in combination with the non-invasive data 169, such as disclosed herein.

The non-invasive measurement control 168 can also be configured to control the data acquisition process (e.g., sample rate, line filtering) for measuring electrical activity and providing the non-invasive measurement data 169 for each of a plurality of locations, which are specified by the geometry data. In some examples, the control 168 can control acquisition of measurement data 170 separately from the therapy system operation, such as in response to a user input. In other examples, the measurement data 170 can be acquired concurrently with and in synchronization with delivering therapy, such as to detect electrical activity of the heart 152 that occurs in response to applying a given therapy (e.g., according to therapy parameters) or specific signals applied for purposes of localization. For instance, appropriate time stamps can be utilized for indexing the temporal relationship between the respective measurement data 160 and 169 and delivery of therapy.

The analysis and output system 162 can be programmed to implement an electrogram reconstruction engine 180 and a map generator 182 for producing electroanatomic maps. By way of example, electrogram reconstruction 180 can be programmed to compute an inverse solution and provide corresponding reconstructed electrograms (e.g., corresponding to non-invasive electroanatomic data 12 or 60) based on the non-invasive data 169 and the geometry data 172. The geometry data 172 that is utilized by the electrogram reconstruction 180 can correspond to actual patient anatomical geometry, a preprogrammed generic model or a combination thereof (e.g., a model that is modified based on patient anatomy). The reconstructed electrograms thus can correspond to electrocardiographic activity across a cardiac envelope, and can include static (three-dimensional at a given instant in time) and/or be dynamic (e.g., four-dimensional map that varies over time).

Examples of inverse algorithms that can be utilized by the reconstruction engine 180 in the system 150 include those disclosed in the U.S. Pat. Nos. 7,983,743 and 6,772,004, which are incorporated herein by reference. The reconstruction engine 180 thus can reconstruct the body surface electrical activity measured via the sensor array 164 onto a multitude of locations on a cardiac envelope (e.g., greater than 1000 locations, such as about 2000 locations or more). In other examples, the analysis and output system 162 can compute electrical activity over a sub-region of the heart based on electrical activity measured directly and invasively, such as via the device 156 (e.g., including a basket catheter or other form of measurement probe). As mentioned, the direct measurements may also constrain the computation implemented by the reconstruction 180.

As a further example, the geometry data 172 that is utilized by the reconstruction engine 180 may include a graphical representation of the patient's torso, such as image data acquired for the patient. For example, the geometry data 172 can be acquired using nearly any imaging modality (e.g., CT, MRI, ultrasound, xray or the like) based on which the corresponding representation of the cardiac envelope can be constructed, such as described herein. Such imaging may be performed concurrently with recording the electrical activity that is utilized to generate the electrical measurement data 170 or the imaging can be performed separately (e.g., before or after the measurement data has been acquired). For instance, such image processing can include extraction and segmentation of anatomical features, including one or more organs and other structures, from a digital image set. Additionally, a location for each of the electrodes in the sensor array 164 can be included in the geometry data 172, such as by acquiring the image while the electrodes are disposed on the patient and identifying the electrode locations in a coordinate system through appropriate extraction and segmentation. Other non-imaging based techniques can also be utilized to obtain the position of the electrodes in the sensor array in the coordinate system, such as a digitizer or manual measurements.

The geometry data 172 can further correspond to a mathematical model, such as can be a generic model or a model that has been constructed based on image data for the patient. Appropriate anatomical or other landmarks, including locations for the electrodes in the sensor array 164 can be identified in the geometry data 172 for display in conjunction with computed location information for the device. The identification of such landmarks and can be done manually (e.g., by a person via image editing software) or automatically (e.g., via image processing techniques).

The output system 162 can generate corresponding output data 174, based on the electrical measurement data (e.g., noninvasive data 169 and/or intracardiac data 160), which output data that can in turn be rendered as a corresponding graphical output in a display 192, such as including electrical activity reconstructed on the cardiac envelope or electrical characteristics derived from such reconstructed electrical activity, as mentioned above. The electrical activity or derivations thereof can be displayed on graphical model of patient anatomy or superimposed on the electrocardiographic map 194.

The output system 162 may also generate an output to identify a location of the device 156 based on coordinates determined by the localization engine 188. The output data 174 can represent or characterize the position of the device 156 in three-dimensional space based on coordinates determined according to any of the approaches herein. Additionally, the location (or a corresponding path) can be displayed at the spatial locations across a cardiac envelope (e.g., on an epicardial or endocardial surface of the heart 152). The output system 162 can display the location separately. In other examples, the location can be combined with other output data, such as to display location information on graphical map of electrical activity of the heart 152, such as a with respect to the locations of one or more zones.

Additionally, in some examples, the output data 174 can be utilized by the system 158 in connection with controlling delivery of therapy or monitoring electrical characteristics. The controls 159 and/or 161 implemented by the intracardiac system 158 can be fully automated control, semi-automated control (partially automated and responsive to a user input) or manual control based on the output data 174. In some examples, the control 160 of the therapy system can utilize the output data to control one or more therapy parameters. In other examples, an individual can view the map generated in the display to manually control the therapy system at a location determined based on this disclosure. Other types of therapy and devices can also be controlled based on the output data 174 and corresponding graphical map 194.

As disclosed herein, the analysis and output system 162 includes a zone analyzer 184 to identify on or more zones that contain one or more mechanisms of distinct arrhythmogenic electrical activity. The zone analyzer 184 can be implemented, for example, as corresponding to the mechanism analyzer 16 or 64 disclosed herein. Thus, the zone analyzer 182 can identify one or more zones as well as identify the number or types of mechanisms of distinct arrhythmogenic electrical activity that have been identified. The zone analyzer further can provide other information (e.g., statistics) computed for each respective zone based on the non-invasive data 169.

The analysis and output system 162 can also include an intracardiac analyzer 185, which can correspond to the intracardiac analyzer 22 or 78 disclosed herein. The intracardiac analyzer 185 thus can be programmed to determine intracardiac signal characteristics (e.g., cycle length, cycle length variation, fractionation, percent of continuous activation as well as various statistics thereof determined individually or in combination) based on analysis of the intracardiac data 160. A priority calculator 186 can be programmed to determine priority of respective spatial regions and/or local sites with respective zones based on the zone analysis 184 and intracardiac analysis 185. The analysis and output system 162 can in turn provide the output data 174 based on the zone analyzer 184, intracardiac analyzer 185 and/or priority calculator 186, such as disclosed herein. For example, the output data 174 can include an indication of priority (e.g., zonal priority among identified zones and/or local priority among sites) to facilitate diagnosis and/or treatment of the respective sites within each of the zones where mechanisms have been identified. In response to updates in some or all of the electrical measurement data 170, the analysis and output system 162 thus can dynamically update the priority information, mechanism data, and intracardiac signal characteristics and generate corresponding updated output data 174.

As disclosed herein, the intracardiac system 158 also includes treatment control 160 that can be utilized to apply treatment to a patient's body via a device 156, which can be automatic control based on the output data, semi-automatic or manual controls in response to user inputs (e.g., via GUI 190). The treatment can include, for example, ablation (e.g., RF ablation, cryoablation, surgical ablation or the like) as well as other forms of treatment disclosed herein. The electrical measurement data 170, including non-invasive data and intracardiac data, can be acquired concurrently (or separately in response to user controls). Additionally, the analysis and output system 162 can evaluate the computed data to ascertain changes in computed zone analysis, intracardiac analysis and/or priority, which changes can be provided in the output data 174 (e.g., based on comparisons by evaluator 102) to provide useful clinical data to facilitate the diagnosis and treatment process.

Figure 6:
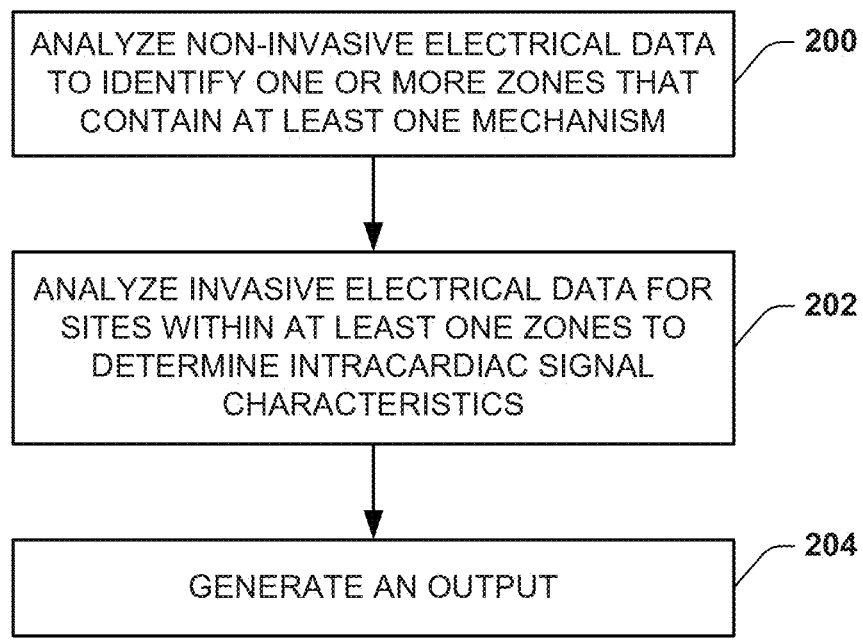
FIG. 6 is a flow diagram depicting an example of a method.

In view of the foregoing structural and functional features described above, a method that can be implemented will be better appreciated with reference to flow diagram of FIG. 6. While, for purposes of simplicity of explanation, the method of FIG. 6 is shown and described as executing serially, it is to be understood and appreciated that such methods are not limited by the illustrated order, as some aspects could, in other examples, occur in different orders and/or concurrently with other aspects from that disclosed herein. Moreover, not all illustrated features may be required to implement a method. The methods or portions thereof can be implemented as instructions stored in a non-transitory machine readable medium as well as be executed by a processor of one or more computer devices, for example.

At 200, the method includes analyzing non-invasive electrical data for a region of interest (ROI) of a patient's anatomical structure (e.g., by mechanism analyzer 16 or 64) to identify one or more zones within the ROI that contain at least one mechanism of distinct arrhythmogenic electrical activity. At 202, the method also includes analyzing invasive electrical data for a plurality of signals of interest at different spatial sites within each of the identified zones (e.g., by intracardiac analyzer 22 or 78) to determine intracardiac signal characteristics for the plurality of sites within each respective zone. At 204, one or more outputs (e.g., output data 20 or 76) can be generated (e.g., by output generator 18) that integrates the at least one mechanism of distinct arrhythmogenic electrical activity for the one or more zones with intracardiac signal characteristics for the plurality of sites within each respective zone.

One or more of the foregoing can be repeated. In some examples, the method can also determine a priority for the plurality of sites within each zone can be determined (e.g., prioritization engine 26 or 94) based on the at least one mechanism of distinct arrhythmogenic electrical activity contained in each respective zone and the intracardiac signal characteristics determined for the plurality of sites within each respective zone. Additionally, a user can employ comparative information provided in the output data based on comparison of mechanism analysis data, intracardiac signal characteristic data and/or priority information that is determined (e.g., by evaluator 102) for different time intervals for the common spatial locations. Thus, clinically relevant and accurate global and local information can be combined to facilitate diagnosis and treatment of irregular cardiac electrical activity.

Additional Examples

The following description provides additional examples of information that can be derived based on integrating non-invasive and invasive electrical information as disclosed herein. The information that is derived can be provided as output data (e.g., output data 20 or 76) for visualization on a display or other output device. Such information for common spatial areas can also be stored in memory for different time intervals evaluated (e.g., by evaluator 102) for different time intervals.

Cycle Length (CL) Mapping:

The output generator 18 or 162 can generate Cycle length 3D map: A local cycle length can be determined by detecting consecutive activation times or via phase processing for non-uniform cycle length electrograms. The local cycle lengths at each point can be aggregated and presented as a 3D map. The Cycle length 3D map can be calculated and presented real-time, or on demand at each salient event during a procedure. The values can be calculated and plotted as a graph at set times or continuously through-out out the procedure. For example, the values can be calculated to provide a baseline value, after each target ablation, after all ablations.

As a further example, the global cycle length of each atrium or both atria together can be calculated by estimating the mean or median of all local CL. Global cycle length information could be calculated using the frequency spectrum and characterizing key components (width of frequency range, prominent frequencies defined by amplitude cutoff, etc). This can be done from all or select channels from the vest signal, representing various parts of the heart. This value or changes in this value ('delta') from previous time-point or event in the procedure can be displayed live or on-demand or at set times throughout procedure.

Cycle Length at Selected Sites:

A selected set of sites that allow stable catheter placement and are more or less stable in rhythm have been used during ablation as 'sentinel' sites to provide a representation of real-time changes in CL during an fibrillation ablation procedure. It provides an indicator of how the whole atria is responding in CL to the procedure.

Figure 7:
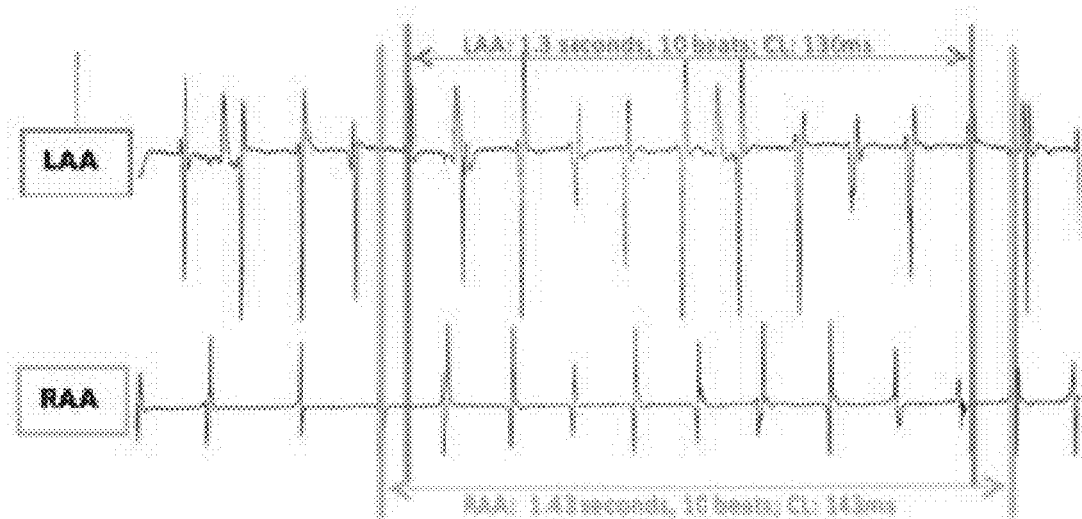
FIG. 7 is an example of a graphical map demonstrating signals acquired for the left atrial appendage and the right atrial appendage.

In FIG. 7, an example of SOIs are shown using RAA and LAA as sentinel sites is shown. The CL values can be extracted from invasive and/or noninvasive electrograms, such as disclosed herein, and displayed real-time or on-demand as CL values on 3D geometry. As one example, the CL values could be extracted using only non-invasive signals that are representative of a given zone, based on geometry data relating sensor locations to patient anatomy. The CL change ('delta') from another time point in the procedure, e.g. change in CL from baseline after pulmonary vein isolation or first target ablation can also be displayed on-demand or real-time. The values can be calculated and plotted as a graph at set times or continuously through-out out the procedure.

Figure 8:
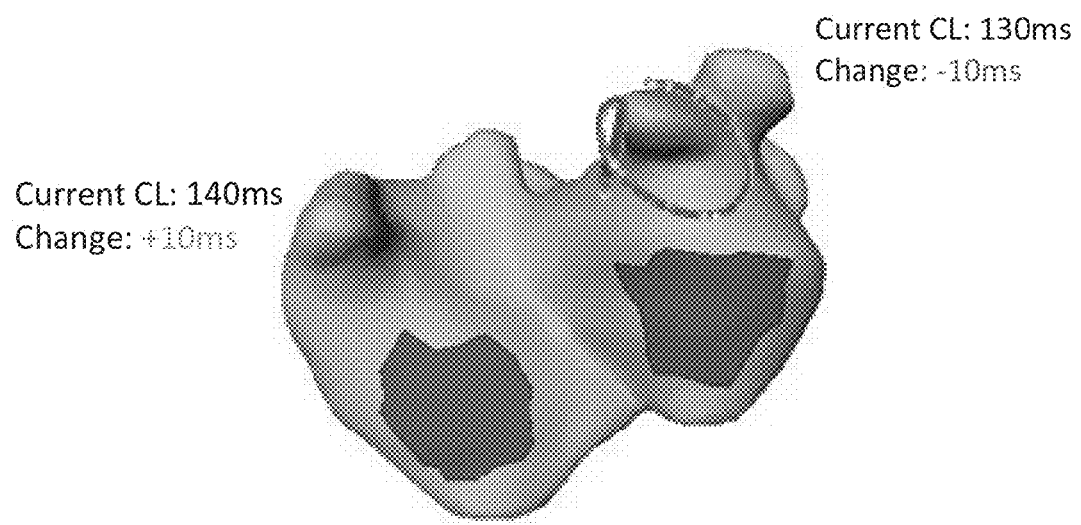
FIG. 8 depicts an example of a graphical map of the heart demonstrating change in cycle length.

An example 3D map for this concept is shown in FIG. 8 demonstrating current CLs at two locations along with corresponding CL change (e.g., deltas). Additionally, or alternatively, the CL can be measured and displayed with a roving catheter that contacts tissue for a period of time (e.g., measurement interval) to calculate each local CL at a given site, before moving on to a different location.

Figure 9A:
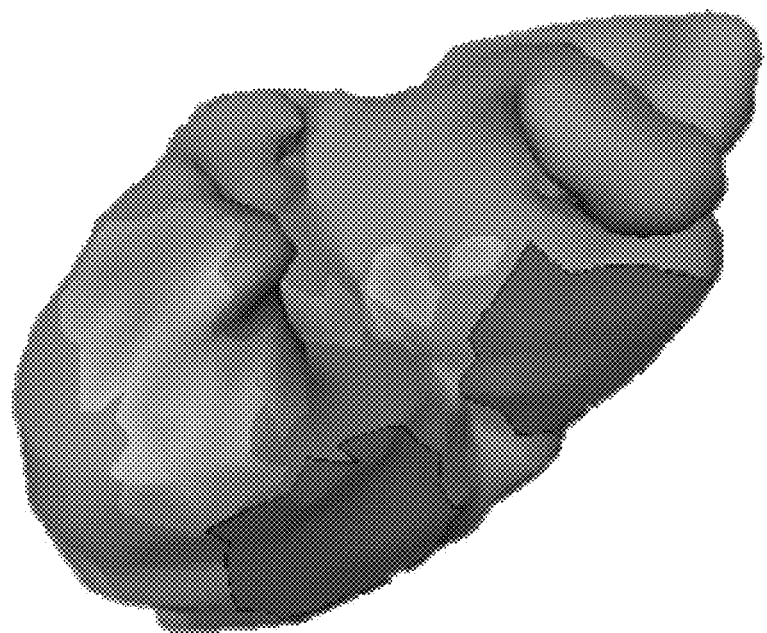
FIG. 9A depicts an example of a graphical map demonstrating changing signals from the right atrium (RAd and RAp).
Figure 9B:
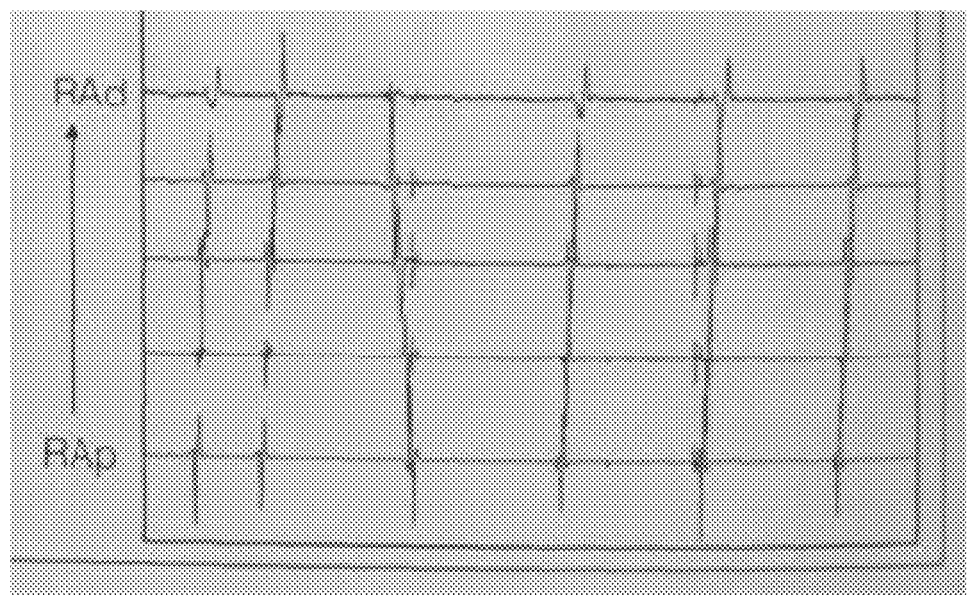
FIG. 9B depicts an example of associated signals demonstrating changing signals from the right atrium (RAd and RAp).

Atrial Conduction Mapping & Tracking:

Conduction patterns derived from invasive data measured using various catheters can be detected and merged with information from noninvasive mapping information to provide integrated information, such as can include vectors, annotations and other visualization to help the diagnosis of complex arrhythmias, such as including during fibrillation. The integrated information can be used, for example, to detect and present electrical activation patterns, and a consistency index of these patterns, over time. An example of merged conduction patterns is demonstrated in FIGS. 9A and 9B.

Atrial Synchrony Mapping:

The concept of local and global cycle length mapping can be further extended to the monitor bi-atrial synchrony. During atrial fibrillation, the global cycle length is constantly varying. For instance, during the ablation procedure, transient organization of one or both chambers could happen, but with a gradient of CL between the two atria. During atrial tachycardia, both atrial have the same fast and organized cycle length. Thus, the comparison in timing (e.g., CL between the two atria or bi-atrial synchrony) can be calculated as a parameter and displayed to understand bi-atrial rhythms and associated changes with salient events including ablation during a procedure. The CL between atria and/or bi-atrial synchrony can be utilized to compute an atrial synchrony index, which can be evaluated relative to a threshold set to quantify patient's synchrony on a relative scale. Cycle length information can also be characterized using frequency components of the vest signals.

Additionally, intra and inter atrial synchrony can be calculated and displayed both live, on-demand, and at set times throughout a procedure. The method can also detect and present % of time each individual atrium is organized (e.g., synchronous). The method can also detect and present % of time both atria are organized (e.g., synchronous). The synchrony measurements also can be expressed as a gradient between points or chambers. This information can be presented as an index (e.g., an atrial organization index) that can be used to demonstrate, for example, if one chamber has a constant delay overall compared to one or more other chambers. For instance, the index can signify that the faster chamber is the driver. The index further can be provided as an input to prioritizing zones. For example, if the number of mechanisms is equal between zone 1 in chamber A and zone 2 in chamber B, respectively, and a computed atrial synchrony index suggests chamber A is faster and/or less synchronous (e.g., more disorganized) relative to chamber B, zone 1 would be assigned (e.g., by prioritization engine 26 or 94) a higher priority than zone 2.

Alternatively, if the gradients are constantly changing, then the index can demonstrate more of a bi-atrial mechanism. Additionally, for simpler arrhythmias, the index can be used to discern which chamber harbors the tachycardia, and which chamber passively conducts.

Figure 10:
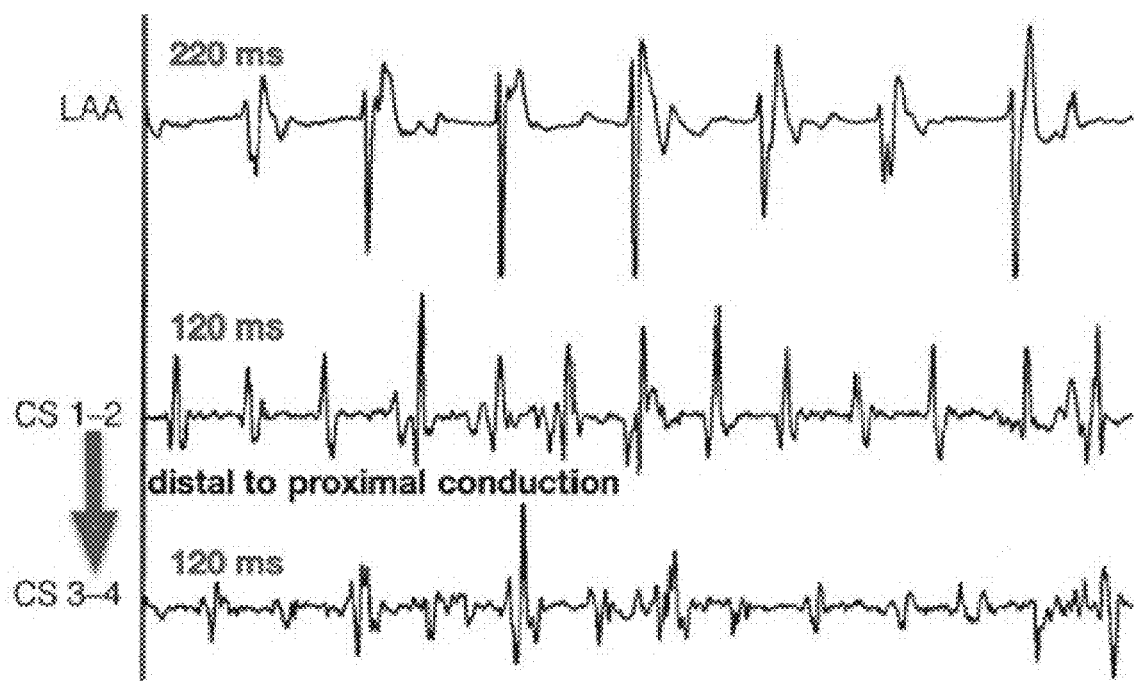
FIG. 10 depicts examples of signals demonstrating different cycle lengths and distal to proximal conduction that can be determined.
Figure 11:
FIG. 11 depicts examples of coronary sinus signals that can be analyzed as disclosed herein.
Figure 12:
FIG. 12 depicts an example of a graph demonstrating coronary sinus signals.

Biatrial Analysis Via Coronary Sinus (CS) Conduction Mapping:

CS catheter signals can be processed to identify activation information, such as distal to proximal or vice versa, chevron, reverse chevron pattern or no pattern/disorganized signals. Examples are demonstrated in FIGS. 10, 11 and 12. Changes in CS conduction patterns can be monitored and conduction direction displayed real-time or on demand and also with changes in salient procedural events such as ablation or other treatments, for example.

CS Organization:

The method can also be implemented to detect when CS signals are substantially perfectly organized vs. not organized. The method can also be programmed to evaluate % of time CS is organized, and display a corresponding organization index over time, such as by color coding in map or other form of visualization, which can be particularly relevant when evaluating local endpoint. For instance, when treating a zone 1) a user can employ the systems and methods disclosed herein to look for improvement on invasive signal measured during and/or after treatment compared to pre-treatment, 2) a remap can be initiated (e.g., in response to user input or automatically) to detect if mechanisms still reside in the zone, 3) the global impact to synchrony can be evaluated during and following treatment, such as by comparing synchrony computed before treatment with intra- and/or post-treatment synchrony. CS organization is a surrogate to global impact. Therefore, in response to observing an acute change to CS organization during zone 1 treatment, the treatment point can be tagged uniquely to reflect global response.

Similar evaluation of CL can be employed. For example, when detect an improvement in synchrony is detected, as defined by CL increase, CL consistency, etc., the treatment point can be tagged according to the global response indicated by changes in CL.

In some examples, CS analysis method can also be programmed to detect when the CS signal is organized compared to other electrograms from salient sites (e.g., selected automatically for anatomical landmarks or in response to a user input). This comparative data can be displayed, such as by color coding in map or other form of visualization.

The CS analysis method can also be programmed to detect CS activation direction and to evaluate % of time activation is Distal to Proximal versus proximal to distal. This determined CS activation information can be displayed, such as by color coding in map or other form of visualization.

The CS analysis method can also be programmed to detect CS activation and evaluate % of time activation has any consistent activation (any of above patterns) vs. no activation organization. This determined CS activation information can be displayed, such as by color coding in map or other form of visualization.

The CS analysis method can also be programmed to provide an alert when CS changes direction (e.g., an audible and/or visual alert indicator). The method can also calculate an index for extent of CS direction change. The computed index can be displayed, such as by color coding in map or other form of visualization.

The CS analysis method can also be programmed to generate an output graphical visualization corresponding each of the above, such as can be presented on a graphical map. The computed information about an attribute or event can be rendered in the a map in one or more forms, such as including vectors, annotations and other dynamic visualization, and further can be provided in real-time or on-demand and with changes during salient events during the procedure like ablation.

The systems and methods disclosed herein can also be programmed to analyze Local or Global rhythm changes while mapping fibrillation including the following:
  i. Detect transient organization (in any catheter or set of catheters or chamber or site).
  ii. Detect change from disorganization to organization (in any catheter or set of catheters or chamber or site).
  iii. Detect change from one organized rhythm to another (AT1 to AT2) (in any catheter or set of catheters or chamber or site)
  iv. An operator alert can also be generated to inform a user one or more of the preceding detected changes related to local or global rhythm changes.

The systems and methods disclosed herein can also be programmed to analyze intermittent pauses/slowing of rate such as can include the following:
  i) Detect transient slowing of rate and/or pause.
  ii) An operator alert can also be generated to inform a user if the rate slows relative to a threshold or a pause is detected.
  iii) Count and display intra-cardiac pause information at given heart locations.

The systems and methods disclosed herein can also be programmed to analyze an acceleration of the rate, such as can include one or more of the following:
  i) Detect cycle length acceleration, or fractionation index acceleration from any catheter.
  ii) An operator alert can also be generated to inform a user if the rate detected by a catheter increases above a threshold.
  iii) Count/display acceleration information at given heart locations.

The systems and methods disclosed herein can also be programmed to analyze the percent of time a given region or location is active in a given cycle, and can include the following:
  iv) Detect percentage of time a signal or region is active across a given cycle
  v) An operator alert can also be generated to inform a user if the % of activation increases or decreases beyond a threshold.
  vi) Count and display % of activation information at given heart locations The systems and methods disclosed herein can also be programmed to analyze sharpness of the signals. For example, the method can determined a deflection frequency, such as a sharpness that can be detected to delineate focal firing or trigger activity from other mechanisms or passive activation. The sharpness of a signal can be detected and displayed (e.g., in map or other visualization) in contrast to neighboring regions.

Atrial Tachycardia Diagnosis:

The systems and methods disclosed herein can also be programmed to detect conduction patterns from various catheters and merge with information from noninvasive mapping information to provide vectors, annotations and other visualization to help the diagnosis of complex arrhythmias like atrial tachycardias.

The systems and methods disclosed herein can also be programmed to analyze biatrial substrate mapping, such as can include one or more of the following:
  a) Detect complex fractionated EGMs—based on voltage, frequency and phase—using intracardiac EGMs
  b) Detect complex fractionated EGMs—based on voltage, frequency and phase using noninvasive electrograms
  c) Detect complex fractionated EGMs—based on voltage, frequency and phase using both intracardiac EGMs and noninvasive electrograms
  d) Detect EGM percentage of continuous activation—based on voltage, % of CL, and phase—using intracardiac EGMs
  e) Fractionation index at a given electrode+delta
  f) % of continuous activation at a given electrode+delta
  g) Organization index at a given electrode+delta
  h) Visualize EGM substrates using above methods—individually or merged with information derived from non-invasively acquired electrical activity (e.g., such as can be provided from a 3D ECVUE software system available from CardioInsight Technologies, Inc. of Cleveland, Ohio)

The following provide common principles applicable for each the concepts disclosed herein disclosure.

1. All analyses can be completely automatic, semi-automatic with or without parameter input from physician/operator
2. All analyses can employ algorithms that operate on one or more intra-cardiac or noninvasive signal.
3. All analyses are applicable for both organized and/or fibrillatory rhythms.
4. All analyses are applicable to atrial or ventricular rhythms, and can be applied to a combination of atrial and ventricular information.

5. Information can be evaluated in a beat to beat fashion for all arrhythmias including fibrillation.

6. The disclosure further describes the acquisition, processing and visualization of signal analysis based on hybrid processing of invasively acquired signals and noninvasively acquired signals. The analysis may result in numerical values or other indicators ('high' 'low' 'decrease' 'increase' 'undetermined' 'no change' etc), which can be displayed as such or visually using graphical descriptors (annotations, arrows, lines of blocks, annotations, flashing indicators etc) on 3D color maps or as color maps themselves. The values can be displayed as a graph to show changes over events or over time.

In view of the foregoing structural and functional description, those skilled in the art will appreciate that portions of the systems and method disclosed herein may be embodied as a method, data processing system, or computer program product such as a non-transitory computer readable medium. Accordingly, these portions of the approach disclosed herein may take the form of an entirely hardware embodiment, an entirely software embodiment (e.g., in a non-transitory machine readable medium), or an embodiment combining software and hardware, such as shown and described with respect to the computer system of FIG. 8. Furthermore, portions of the systems and method disclosed herein may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of structures, components, or methods, but one of ordinary skill in the art will recognize that many further combinations and permutations are possible. Accordingly, the invention is intended to embrace all such alterations, modifications, and variations that fall within the scope of this application, including the appended claims. Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. A method, comprising:
receiving, by a system comprising a processor, non-invasive electrical data from a plurality of electrodes on an external surface of a patient's body, wherein the plurality of electrodes define a region of interest (ROI) of the patient's anatomical structure;
analyzing, by the system, the non-invasive electrical data for the ROI to identify one or more zones within the ROI that contain at least one mechanism of distinct arrhythmogenic electrical activity;
analyzing, by the system, invasive electrical data for a plurality of signals of interest at different spatial sites within each of the identified one or more zones to determine intracardiac signal characteristics for the different spatial sites within each of the identified one or more zones;
generating, by the system, output data that integrates the at least one mechanism of distinct arrhythmogenic electrical activity for the one or more zones with the intracardiac signal characteristics for the plurality of sites within each respective zone;
determining, by the system, a baseline indication of synchrony across at least one of the respective zones based on the output data;
determining, by the system, a post-treatment indication of synchrony across the at least one of the respective zones after applying a treatment to at least one of the plurality of sites based on the output data that is recalculated after application of the treatment;
comparing, by the system, the baseline indication of synchrony with the post-treatment indication of synchrony and providing a comparison output indicating changes between the baseline indication of synchrony and the post-treatment indication of synchrony; and
displaying, by a display device of the system, a visualization based on the comparison output.

2. The method of claim 1, wherein analyzing non-invasive electrical information further comprises determining a number of mechanisms of distinct arrhythmogenic electrical activity that occur within each respective zone during at least one time interval.

3. The method of claim 2, wherein the number of mechanisms of distinct arrhythmogenic electrical activity within each respective zone comprises at least one of a number of rotors that occur within the at least one time interval or a number of foci that occur within the at least one time interval, and a number of fast bursting cycle length that occur within the at least one time interval.

4. The method of claim 2, wherein the one or more zones are a plurality of zones, the method further comprises: determining a zonal priority among the plurality of zones based on a relative number of the mechanisms of distinct arrhythmogenic electrical activity that occur within in each respective zone during the at least one time interval.

5. The method of claim 4, further comprising evaluating a plurality of different intracardiac signal characteristics determined for the plurality of sites within each zone to determine a local priority among the plurality of sites within each respective zone.

6. The method of claim 5, wherein the plurality of different intracardiac signal characteristics comprises at least two of a cycle length, cycle length variation, percentage of continuous activation and fractionation determined for at least one measurement interval.

7. The method of claim 6, further comprising assigning different priority weighting to at least two of the different intracardiac signal characteristics for the plurality of sites within a given zone according to the mechanisms of distinct arrhythmogenic electrical activity identified for the given zone to provide weighted signal characteristics for the at least two different intracardiac signal characteristics, and wherein the local weighting for the plurality of sites within the given zone is determined based on the weighted signal characteristics for the given zone.

8. The method of claim 7, wherein the mechanisms of distinct arrhythmogenic electrical activity within the given zone comprise at least one of rotors that occur within the at least one time interval, foci that occur within the at least one time interval or a cycle length determined for the at least one time interval to be below a predetermined threshold, wherein in response to determining that the only mechanisms of distinct arrhythmogenic electrical activity in the given zone include one or more rotors, the method comprising assigning a greater priority weighting to the percentage of continuous activation relative to other intracardiac signal characteristics determined for the at least one measurement interval and for the given zone, and wherein in response to determining that the only mechanisms of distinct arrhythmogenic electrical activity in the given zone include one or more foci, the method comprising assigning an increased priority weighting to at least one of cycle length or the cycle length variation relative to the other intracardiac signal characteristics determined for the at least one measurement interval and for the given zone.

9. The method of claim 7, wherein the mechanisms of distinct arrhythmogenic electrical activity within each respective zone comprise at least two of rotors that occur within the at least one time interval, foci that occur within the at least one time interval or cycle length determined for the at least one time interval to be below a predetermined threshold, and wherein each of the intracardiac signal characteristics determined for the given zone are weighted proportionally to the number of each type of the mechanisms of distinct arrhythmogenic electrical activity identified within the given zone.

10. The method of claim 1, further comprising generating a hybrid graphical map of the ROI of the patient's anatomical structure, the hybrid map integrating the non-invasive electroanatomic data and the intracardiac signal characteristics determined for at least a portion of the plurality of sites.

11. A system, comprising:
an arrangement of sensors configured to measure electrical data from an external body surface;
a device configured to measure electrical activity directly from a cardiac surface;
memory configured to store non-invasive electroanatomic data representing cardiac electrical activity reconstructed on a cardiac envelope based on the electrical data from the arrangement of sensors, intracardiac electrical data based on the electrical activity measured by the device invasively measured electrical data for a plurality of sites, and machine readable instructions;
a processor configured to execute the machine readable instructions the instructions comprising:
providing zone data identifying one or more zones within a region of interest of the cardiac envelope that contain at least one mechanism of distinct arrhythmogenic electrical activity based on the non-invasively sensed electrical data;
determining intracardiac signal characteristic data representing intracardiac signal characteristics based on the intracardiac electrical data for a plurality of sites within each respective zone; and
providing output data that integrates the zone data and the intracardiac signal characteristic data; and
determining (i) a baseline indication of synchrony across one of the zones based on the output data measured prior to delivery of a treatment and (ii) another indication of synchrony across the one of the zones based on the output data obtained during or after delivery of a treatment to one or more sites within the one of the zones; and
comparing the baseline indication of synchrony with the other indication of synchrony; and
providing a comparison output indicating changes between the baseline indication of synchrony and the other indication of synchrony;
a display device configured to display a visualization based on the comparison output.

12. The system of claim 11, wherein the instructions further comprising determining a priority for the plurality of sites within each zone based on the at least one mechanism of distinct arrhythmogenic electrical activity contained in each respective zone and the intracardiac signal characteristic data for the plurality of sites within each respective zone.

13. The system of claim 12, wherein the one or more zones are a plurality of zones, wherein the instructions further comprise:
determining a zonal priority among the plurality of zones based on a relative number of the mechanisms of distinct arrhythmogenic electrical activity that occur within in each respective zone during at least one time interval; and
determining a local priority among the plurality of sites within each respective zone based on the plurality of different intracardiac signal characteristic data.

14. The system of claim 13, wherein the instructions further comprise assigning different priority weighting to at least two of the intracardiac signal characteristics for the plurality of sites within a given zone according to the mechanisms of distinct arrhythmogenic electrical activity identified for the given zone to provide weighted signal characteristics for the at least two different intracardiac signal characteristics, and determining the local priority among the plurality of sites within the given zone based on the weighted signal characteristics for the given zone.

15. The system of claim 11, wherein the instructions further comprise:
identifying one or more rotors that occur on the cardiac envelope within at least one time interval based on the non-invasive electroanatomic data;
to identifying one or more foci that occur on the cardiac envelope within the at least one time interval based on the non-invasive electroanatomic data; and
determining each of the one or more zones based on the rotors and foci identified for each respective zone.

16. The system of claim 11, wherein the output data includes baseline output data prior to delivery of a given treatment, the system further comprising an intracardiac system including a treatment control to deliver a treatment via a device, wherein the instructions further comprise providing zone data identifying one or more zones within a region of interest of the cardiac envelope that contain at least one mechanism of distinct arrhythmogenic electrical activity based on the non-invasively sensed electrical data obtained during or after the delivery of the treatment; and wherein the instructions determine the intracardiac signal characteristic data representing intracardiac signal characteristics based on the intracardiac electrical data obtained during or after the delivery of the treatment.

17. The system of claim 16, wherein the zone data and intracardiac signal characteristic data determined from data during or after the delivery of the treatment are treatment output data, wherein the instructions further comprise comparing the baseline output data with the treatment output data to provide a comparison output indicating changes between the baseline output data and the treatment output data.

\* \* \* \* \*